US012636520B2

(12) United States Patent
Fu et al.

(10) Patent No.: US 12,636,520 B2
(45) Date of Patent: May 26, 2026

(54) COLLIMATOR APPARATUS AND MOTION CONTROL METHOD

(71) Applicant: JIANGSU RAYER MEDICAL TECHNOLOGY CO., LTD., Wuxi (CN)

(72) Inventors: Dongshan Fu, Wuxi (CN); Xueguo Cao, Wuxi (CN); Fu Zhang, Wuxi (CN); Jingxian Zhang, Wuxi (CN); Jingjing Zhao, Wuxi (CN)

(73) Assignee: JIANGSU RAYER MEDICAL TECHNOLOGY CO., LTD, Wuxi (CN)

( * ) Notice: Subject to any disclaimer, the term of this patent is extended or adjusted under 35 U.S.C. 154(b) by 0 days.

(21) Appl. No.: 18/574,778

(22) PCT Filed: Jan. 13, 2023

(86) PCT No.: PCT/CN2023/072061
§ 371 (c)(1),
(2) Date: Dec. 28, 2023

(87) PCT Pub. No.: WO2023/134741
PCT Pub. Date: Jul. 20, 2023

(65) Prior Publication Data
US 2025/0001210 A1 Jan. 2, 2025

(30) Foreign Application Priority Data

Jan. 17, 2022 (CN) .......................... 202210045978.4
Dec. 7, 2022 (CN) ........................ 202211580708.X

(51) Int. Cl.
*A61N 5/10* (2006.01)

(52) U.S. Cl.
CPC ......... *A61N 5/1045* (2013.01); *A61N 5/1049* (2013.01); *A61N 5/1075* (2013.01)

(58) Field of Classification Search
None
See application file for complete search history.

(56) References Cited

U.S. PATENT DOCUMENTS 5,945,684 A * 8/1999 Lam .......................... G21K 1/04
378/65
2013/0261430 A1 10/2013 Uhlemann
(Continued)

FOREIGN PATENT DOCUMENTS

CN 2213545 Y 11/1995
CN 2526031 Y 12/2002
(Continued)

OTHER PUBLICATIONS

Translated Chinese Office Action, App. No. 202210045978.4, dated Oct. 14, 2022, pp. 1-10.
(Continued)

*Primary Examiner* — Hoon K Song
(74) *Attorney, Agent, or Firm* — BOND, SCHOENECK & KING, PLLC; George R. McGuire

(57) ABSTRACT

Provided are a collimator apparatus and a motion control method. The collimator apparatus includes a transmission assembly and at least two collimators. The transmission assembly is connected to the at least two collimators. The transmission assembly is configured to implement automatic switching of different collimators through rotation action.

21 Claims, 15 Drawing Sheets

(56) References Cited

U.S. PATENT DOCUMENTS

| | | | |
|---|---|---|---|
| 2014/0048727 A1 | 2/2014 | Huntzinger et al. | |
| 2018/0206806 A1 | 7/2018 | Jenkins et al. | |
| 2018/0318607 A1 | 11/2018 | Wilbur et al. | |
| 2019/0272928 A1* | 9/2019 | Singer | G01N 23/20091 |
| 2020/0304045 A1 | 9/2020 | Ye et al. | |

FOREIGN PATENT DOCUMENTS

| CN | 201291000 | Y | 8/2009 |
|---|---|---|---|
| CN | 101548201 | A | 9/2009 |
| CN | 102755696 | A | 10/2012 |
| CN | 106512221 | A | 3/2017 |
| CN | 108079444 | A | 5/2018 |
| CN | 108096720 | A | 6/2018 |
| CN | 108744315 | A | 11/2018 |
| CN | 109069086 | A | 12/2018 |
| CN | 109925608 | A | 6/2019 |
| CN | 209405502 | U | 9/2019 |
| CN | 110404181 | A | 11/2019 |
| CN | 111141763 | A | 5/2020 |
| CN | 214807946 | U | 11/2021 |
| CN | 114452549 | A | 5/2022 |
| CN | 217187511 | U | 8/2022 |
| CN | 217430684 | U | 9/2022 |
| JP | S623679 | A | 1/1987 |
| JP | H0739595 | A | 2/1995 |
| WO | 2016175360 | A1 | 11/2016 |
| WO | 2019136698 | A1 | 7/2019 |
| WO | 2021087681 | A1 | 5/2021 |

OTHER PUBLICATIONS

Translated Chinese Office Action, App. No. 202211580708.X, dated Aug. 16, 2023, pp. 1-20.

Translated International Search Report, Application No. PCT/CN2023/072061, prepared Mar. 13, 2023, mailed Mar. 22, 2023, pp. 1-5.

EP Partial Supplementary Search Report, Application No. 23740082.5, dated Aug. 12, 2024, entire document.

EP Search Report; Application No. 23740082.5-1122; Dated Oct. 28, 2024, Entire document.

* cited by examiner

COLLIMATOR APPARATUS AND MOTION CONTROL METHOD

CROSS-REFERENCE TO RELATED APPLICATION

This is a National stage application, filed under 37 U.S.C. 371, of International Patent Application NO. PCT/CN2023/ 072061, filed on Jan. 13 2023, which claims priority to Chinese Patent Application No. 202210045978.4 filed with the China National Intellectual Property Administration (CNIPA) on Jan. 17, 2022 and claims priority to Chinese Patent Application No. 202211580708.X filed with the CNIPA on Dec. 7, 2022, the disclosures of which are incorporated herein by reference in their entireties.

TECHNICAL FIELD

The present disclosure relates to the technical field of radiosurgery robotic devices, for example, a secondary collimator apparatus capable of implementing automatic and quick switching and a motion control method.

BACKGROUND

Image-guided radiation therapy (IGRT) is a new technology of tumor radiation therapy that is gradually developed. Through an advanced imaging device and an image processing method, in a treatment planning stage, an accurate target area detection and delineation, distribution planning of treatment radiation beams, and dose distribution calculation are performed on a patient, accurate target area positioning is performed before treatment irradiation, and target area motion tracking is performed during treatment. In this manner, accurate radiation therapy for a tumor is implemented, and damage to normal tissues and key organs around a tumor is reduced. Image-guided technology is the basis for modern emerging accurate radiation therapy, such as stereotactic radiosurgery surgery (SRS) of the head and neck and stereotactic body radiotherapy (SBRT). Accurate radiation therapy SRS and SBRT are also collectively referred to as radiosurgery.

A radiosurgery robotic system is a special device for radiosurgery and is mainly applied to accurate radiation therapy of whole-body solid tumors. Combined with advanced technologies such as multimodal image guidance, a modern robot and a miniaturized linear accelerator, accurate radiation therapy under accurate image guidance is implemented. Tumors of different sizes are treated with large doses and low fractions (1 to 5 times).

In a radiosurgery robotic system, multi-beam non-coplanar high-dose small-field irradiation is used in a spherical treatment space. Thus, an accelerator treatment beam can be projected to a target area of a patient in different directions at different positions on the spherical surface to achieve optimal treatment dose distribution and obtain the best treatment effect. A sphere is defined with the treatment center of the radiosurgery system as a sphere center and a source-axis distance (SAD) as a radius. Multiple uniformly distributed nodes (possibly as many as thousands) are planned on the sphere. These nodes are called treatment nodes. A set of all the treatment nodes on the sphere is the spherical treatment space. A treatment planning system selects optimal treatment nodes (tens to hundreds) for the patient from the spherical treatment space to meet the clinical requirements of the optimal dose distribution. Each fractional treatment usually needs the use of multiple fields with different apertures to implement the dose distribution in the treatment plan. Each fractional treatment needs the use of multiple fields with different apertures for irradiation, which can be implemented by replacing with secondary collimators having different apertures in a linear accelerator.

When a circular collimator is used on a radiotherapy device, only one collimator is mounted at a time. A robotic radiosurgery accelerator system is mainly used for stereotactic radiotherapy. Generally, multiple collimators with different apertures are used to complete the treatment plan of the robotic radiosurgery accelerator system. In the treatment process, even if a collimator is automatically replaced by a robot, time is delayed, and work efficiency is reduced.

To solve the problems of time delay and efficiency reduction caused by replacing collimators, in Chinese Patent Application No. 201711349474.7, a collimator is provided. The collimator includes a sliding plate mounted on a fixing plate, a collimator wheel mounted on the sliding plate, and a rotation driving apparatus. The rotation driving apparatus drives the collimator wheel to rotate. The collimator wheel is provided with at least two openings with different sizes along a circumferential direction. The center of the circumference where the openings are located is located on the rotation axis of the collimator wheel. An object of this Patent Application is to quickly implement the replacement of openings with different sizes. Since a collimator wall needs a certain thickness in the treatment process to prevent leakage, the provision of at least two openings with different sizes on one collimator results in a large design volume, overweight of the collimator, potential safety hazards, and inconvenience in the movement of a robot. A motor carries a synchronous belt to move. The synchronous belt is low in transmission precision, easy to age, large in deformation amount, poor in positioning precision, and does not meet clinical use requirements.

In Chinese Patent Application No. 94247384.1, a solution similar to the solution in Chinese Patent Application No. 201711349474.7 is provided. Eccentric collimation holes with different apertures are formed in the cylinder of a collimator. The rotation angle of the cylinder of the collimator is changed by an indexing transmission mechanism to allow the collimation holes with different apertures to be butted with a ray channel, thereby implementing the transformation of ray beam diameters. The preceding design also has problems of huge volume and complex driving of a transmission apparatus.

In Chinese Patent Application No. 200780044846.3, an automatic collimator replacement apparatus is provided. One or more collimators of a radiotherapy system are automatically replaced by a manipulator in a plug-in replacement manner. The automatic collimator replacement system needs to rely on the manipulator. In each replacement, the manipulator needs to leave a treatment position to implement certain movements, that is, grasping a collimator, tightening the collimator, and other movements. When a collimator is replaced, the manipulator returns to the treatment position. This can lead to poor repeated positioning accuracy and prolonged treatment time of each fraction. At the same time, the manipulator also causes certain potential safety hazards to a patient during the movement.

At the same time, during the whole process of radiotherapy, a magnetron continuously outputs microwaves. This can accelerate stray electrons in an acceleration tube, resulting in the generation of a low-energy ray which is a dark current. The dark current is an objective phenomenon. An accelerator has no protection against the dark current, and the dark current can directly irradiate into a patient, thereby resulting in irradiation beyond a treatment plan.

SUMMARY

The present disclosure provides a secondary collimator apparatus capable of implementing automatic and quick switching and a motion control method. At least two collimators are mounted on a treatment head at the same time. During a treatment process, the treatment head can quickly switch collimators according to a treatment plan. In most cases, a collimator can be replaced without stopping the treatment. In this manner, the disadvantage of time delay in replacing the collimators in the related art is overcome.

The present disclosure provides a collimator apparatus. The collimator apparatus includes a transmission assembly and at least two collimators. The transmission assembly is connected to the at least two collimators, and the transmission assembly is configured to implement automatic switching of different collimators through rotation action.

In an embodiment, the collimator apparatus further includes at least two assembly components. Each of the at least two assembly components is provided with a respective one of the at least two collimators, the transmission assembly is connected to the each of the at least two assembly components, the transmission assembly is configured to drive different assembly components through rotation to implement automatic switching of different collimators.

The transmission assembly includes a rotation seat assembly, a fixing seat, a motor assembly, and an electromagnetic pin assembly. The motor assembly and the fixing seat are connected to the rotation seat assembly, the fixing seat is provided with a beam hole, and the rotation seat assembly is configured to, under driving of the motor assembly, drive the at least two assembly components to move to rotate a designated one of the at least two collimators to a position facing the beam hole.

The electromagnetic pin assembly is configured to automatically position, identify, and lock the rotation seat assembly, the electromagnetic pin assembly includes an electromagnetic pin, a mounting ring, and first micro switches; the electromagnetic pin is fixed to the rotation seat assembly by the mounting ring and rotates with the rotation seat assembly, the electromagnetic pin is energized in a case where the motor assembly drives the rotation seat assembly to rotate, and a metal rod of the electromagnetic pin retracts into the electromagnetic pin; the electromagnetic pin is de-energized in a case where the motor assembly has driven the rotation seat assembly to rotate to a desired position, and the metal rod extends out of the electromagnetic pin and is inserted into a tapered hole of the fixing seat so that the rotation seat assembly is not allowed to rotate; and the metal rod is in contact with one of the first micro switches at a corresponding position, the one of the first micro switches is triggered, and in the case where the one of the first micro switches is triggered, the one of the first micro switches is configured to send an electrical signal to allow a system to identify a type of one of the at least two collimators facing a center of the beam hole.

In an embodiment, the collimator apparatus further includes an adjustment frame assembly. The adjustment frame assembly includes a connection plate, a screw, and a nut, the connection plate is configured to connect the transmission assembly to an end of a primary collimator, and in a case where the screw and the nut are adjusted, and the screw and the nut are configured to adjust a distance of the respective one of the at least two collimators on the each of the at least two assembly components to a target point. The respective one of the at least two collimators on the each of the at least two assembly components is a secondary collimator.

In an embodiment, the rotation seat assembly includes a rotation seat, a bearing inner race end cap, two thin-wall bearings, and a bearing outer race end cap.

The two thin-wall bearings are mounted between the rotation seat and the fixing seat, outer walls of the two thin-wall bearings are provided with the bearing outer race end cap and the bearing inner race end cap, and the rotation seat is configured to rotate through the two thin-wall bearings under action of the motor assembly.

The outer walls of the two thin-wall bearings, the bearing outer race end cap, and the bearing inner race end cap are configured to fix the two thin-wall bearings; in a case where the at least two collimators are disposed at a lower end of the collimator apparatus, the bearing outer race end cap is configured to bear a gravity of the collimator; and in a case where the at least two collimators are disposed at an upper end of the collimator apparatus, the bearing inner race end cap is configured to bear the gravity of the collimator. The at least two collimators are each a secondary collimator.

In an embodiment, at least one blind-hole collimator and at least two circular holes are disposed on the rotation seat assembly, the at least one blind-hole collimator is mounted on the rotation seat, and the at least two circular holes are equally distributed and configured to fixedly connect the at least two assembly components; the at least one blind-hole collimator is disposed in the middle of two of the at least two circular holes and on a same circumference as the at least two assembly components, and the motor assembly is further configured to, in a non-therapeutic state, drive the rotation seat assembly to rotate to control one of the at least one blind-hole collimator to switch to the position facing the beam hole.

In an embodiment, the electromagnetic pin is a push-pull electromagnetic pin in a normally closed state; in a case where the electromagnetic pin is de-energized, the metal rod keeps a state of extending out of the electromagnetic pin; in a case where the electromagnetic pin is energized, the metal rod retracts into the electromagnetic pin; and a number of the first micro switches is equal to a sum of a number of blind-hole collimators and a number of circular holes, the first micro switches are fixed to the fixing seat, and each of the blind-hole collimators corresponds to a respective one of the first micro switches, and each of the circular holes corresponds to a respective one of the first micro switches.

The motor assembly includes a motor bracket, a stepper motor, and a coupling; and the stepper motor is mounted on the motor bracket and connected to the coupling, and the coupling is connected to the rotation seat assembly.

In an embodiment, each of the at least two assembly components further includes a collimator identification assembly and a locking assembly; and the locking assembly includes a spring, an outer sleeve, an inner tapered sleeve, and a ball, the outer sleeve is fixed with the inner tapered sleeve, the inner tapered sleeve is in contact with the ball, the ball is in contact with a ball groove of the respective one of the at least two collimators, and the spring is disposed below the inner tapered sleeve and is connected to the inner tapered sleeve.

The inner tapered sleeve is provided with three tapered surface portions which are a first tapered surface, a second tapered surface, and a third tapered surface. In a portion where the first tapered surface is disposed, a cross-sectional area of the inner tapered sleeve gradually decreases from up to down; in a portion where the second tapered surface is disposed, a cross-sectional area of the inner tapered sleeve gradually increases from up to down; and in a portion where the third tapered surface is disposed, a cross-sectional area of the inner tapered sleeve gradually decreases from up to down.

The first tapered surface is tangential to the ball when the first tapered surface is in contact with the ball, the second tapered surface is tangential to the ball when the second tapered surface is in contact with the ball, and the ball is tangential to two tapered angles of the ball groove of the respective one of the at least two collimators.

In an embodiment, the locking assembly has a three-stage locking manner includes two-stage mechanical locking and one-stage locking check protection.

A first-stage mechanical locking manner is that in a case where the spring is in a normal work state, the spring is configured to apply a pressure to the inner tapered sleeve to make the ball effectively contact with the first inner tapered surface of the inner tapered sleeve and make the first tapered surface press the ball to lock the respective one of the at least two collimators; and a second-stage mechanical locking manner is that in a case where the spring loses a pulling force to the inner tapered sleeve, the outer sleeve and the inner tapered sleeve move upward, the ball no longer presses the respective one of the at least two collimators, the respective one of the at least two collimators moves downward for a certain distance until the second tapered surface of the inner tapered sleeve re-presses an outermost ball, and the ball re-presses the ball groove of the respective one of the at least two collimators to implement second-stage mechanical locking of the respective one of the at least two collimators so that the respective one of the at least two collimators does not fall off.

The collimator apparatus further includes a position sensor, and the position sensor is disposed at a distance from a metal sheet on the outer sleeve; and the one-stage locking check protection manner is that in a case where the respective one of the at least two collimators is locked and the outer sleeve is pulled along a preset direction, the metal sheet on the outer sleeve approaches the position sensor, and the position sensor is configured to detect the sheet metal so that the collimator is mounted and locked in place. The respective one of the at least two collimators is a secondary collimator, and the preset direction is a direction in which the respective one of the at least two collimators is disengaged from the each of the at least two assembly components.

A collimator mounting and locking manner is that the respective one of the at least two collimators is mounted in the each of the at least two assembly components, the outer sleeve is pulled downward by hand to make the inner tapered sleeve press the ball so that the ball presses a groove of the respective one of the at least two collimators to lock the respective one of the at least two collimators; and in a case of replacing the respective one of the at least two collimators, the respective one of the at least two collimators is held by hand, and the outer sleeve is pushed upwards to make the ball move to release a locking state so that the respective one of the at least two collimators is disengaged from the each of the at least two assembly components.

In an embodiment, the collimator identification assembly includes a concave portion and a convex portion which are disposed on a top surface of a collimator, a probe with a telescoping spring, and a code identification circuit.

The collimator identification adopts a physical code manner, the concave portion or the convex portion is disposed at a corresponding position on the top surface of the collimator, and the probe with the telescoping spring is disposed above the collimator, corresponds to the concave portion and the convex portion, and is configured to detect a corresponding electrical signal; in a case where the concave portion is located below the probe, the probe is not in contact with the collimator, no current passes through the probe, and a voltage signal is 1; and in a case where the convex portion is located below the probe, the probe is in contact with the collimator, a current passes through the probe, and a voltage signal is 0. The collimator is a secondary collimator.

In an embodiment, at different radii of the top surface of the collimator, a number of concave portions and convex portions are machined, the number of concave portions and convex portions are configured to be identified to form a binary code, and different types of collimators use different codes; the probe is disposed on a printed circuit board (PCB), and the code identification circuit is configured to identify a type of the collimator through a code composed of voltage signals.

In an embodiment, a sum of the number of concave portions and the number of convex portions on the top surface of the collimator is 4, the concave portions and the convex portions are configured to be identified to form a 4 bit binary code, and the binary code corresponds to one of 16 collimator types.

In an embodiment, the collimator apparatus further includes a protection disk assembly. The protection disk assembly is disposed on a side of the at least two collimators facing away from the at least two assembly components and has a certain clearance with the at least two collimators without affecting detection of automatic locking of the at least two collimators, and the protection disk assembly is configured to function as protection and load bearing in a case where the at least two collimators fall off.

The protection disk assembly includes a protection disk mounting rod, a protection disk, a protection disk rotation nut, and a second micro switch, the protection disk is disposed between a bottom of the at least two collimators and the protection disk rotation nut, and the second micro switch is disposed in the protection disk mounting rod.

The second micro switch is configured to detect whether the protection disk rotation nut is mounted in place in a case of tightening the protection disk rotation nut, and the protection disk mounting rod is provided with a through hole for a wire of a groove code apparatus of each of the at least two collimators to pass through.

In an embodiment, each of the at least two collimators is provided with a concave portion, a convex portion, and a ball groove; an angle of the ball groove is tangential to a ball configured for locking.

In an embodiment, the transmission assembly includes a rotation seat assembly, a primary position feedback mechanism, and a fixing seat, and the collimator apparatus further includes a secondary position feedback mechanism and a control circuit.

The at least two collimators are each a secondary collimator, and mounted on the rotation seat assembly, and the rotation seat assembly is configured to drive the at least two collimators to rotate to allow a designated one of the at least two collimators to rotate to a position facing a beam hole.

The primary position feedback mechanism includes a rotor position detection sensor, a driver, and a stepper motor, the stepper motor is connected to the rotation seat assembly and configured to drive the rotation seat assembly to rotate under an instruction of the driver, and the rotor position detection sensor is configured to monitor a position of the stepper motor in real time and automatically switch open-loop control and closed-loop control according to a condition.

The secondary position feedback mechanism includes a grating, a reading head, and a data collection and conversion module; and the reading head is configured to read a scale code of the grating and transmit the scale code to the control circuit through the data collection and conversion module.

In an embodiment, the primary position feedback mechanism further includes a motor bracket, a coupling, and an electromagnetic push rod component; and the stepper motor is mounted on the motor bracket and connected to the coupling, and the coupling is connected to the rotation seat assembly.

In an embodiment, the primary position feedback mechanism has a zero-clearance type hard-block zeroing mechanism and a rotation seat bidirectional limit switch detection mechanism, the primary position feedback mechanism is configured to implement calibration of an initial zero position of the rotation seat through a hard block disposed on the fixing seat, and the primary position feedback mechanism is further configured to implement limit protection and alarm functions of the rotation seat through two forward and reverse rotation over-range limit switches disposed on the fixing seat; and the primary position feedback mechanism is further configured to implement programmable control of the driver through a communication interface circuit of an isolated recommended standard RS-485 to complete switching of a station. The station adopts a double-locking manner of motor torque locking and electromagnetic push rod locking.

In an embodiment, a control manner of the primary position feedback mechanism includes an open-loop control and a closed-loop control, use time of the open-loop control is longer than use time of the closed-loop control, and the primary position feedback mechanism is further configured to execute the open-loop control in a case where an action of the stepper motor is detected in real time; and the primary position feedback mechanism is further configured to, in a case of an instruction and a position offset of the stepper motor due to overload, switch the open-loop control to the closed-loop control to correct position and speed.

The secondary position feedback mechanism is configured to add, on a basis of closed-loop positioning operation of the primary position feedback mechanism, the secondary position feedback mechanism as a final closed-loop target to eliminate, on output positioning, the effect of deformation of transmission link between an output shaft of the stepper motor and an end load.

In an embodiment, the collimator apparatus further includes a protection disk mechanism. The protection disk mechanism includes a rotatable multi-leaf protection disk and a proximity switch detector, and the rotatable multi-leaf protection disk is connected to the collimator apparatus through a mechanical quick connection manner and rotatable in an angular direction; in a case where the rotatable multi-leaf protection disk works normally, each leaf of the rotatable multi-leaf protection disk rotates directly below a respective one of the at least two collimators and is configured to prevent the respective one of the at least two collimators from falling off to ground when locking fails; the proximity switch detector is configured to detect that the rotatable multi-leaf protection disk rotates to a work position and to output a corresponding signal; in a case where a collimator needs to be replaced after treatment, each leaf of the rotatable multi-leaf protection disk is rotated to the middle of respective two of the at least two collimators and is configured to no longer block disengagement and entry of the collimator, and the proximity switch detector is further configured to output a corresponding signal in a case where the rotatable multi-leaf protection disk is not detected in the work position; and in a case where the collimator has been replaced, the rotatable multi-leaf protection disk is rotated directly below a collimator to restore a protection function of the collimator, and the proximity switch detector is further configured to detect a signal of the rotatable multi-leaf protection disk being in the work position and output a corresponding signal.

In an embodiment, the driver is an a-STEP driver, the stepper motor is an a-STEP stepper motor, the control circuit is connected to the reading head and the a-STEP driver, and the a-STEP driver is directly connected to the a-STEP stepper motor to control motion of the rotation seat assembly with multiple stations.

The control circuit includes a power module, a communication module, a collimator physical code module, an electromagnetic push rod driving and position feedback module, and a protection disk detection module.

The power module adopts a two-stage isolation mechanism. One stage of isolation mechanism is to isolate power supply from control supply, and the control supply is implemented by DC/DC conversion of the power supply through a step-down isolation DC/DC power supply; and another stage of isolation mechanism is to isolate communication power supply from the control supply, and the communication power supply is implemented by converting the control supply through an isolated communication chip.

The electromagnetic push rod driving and position feedback module is designed by using pulse width modulation (PWM), with a pulse width adjustment range of 0 to 300 μs; the electromagnetic push rod driving and position feedback module is configured to reduce a coil current to 10% of a rated value in time after the electromagnetic push rod is sucked in place at the moment of current opening to allow a coil to work continuously; through adjusting a PWM duty cycle in real time in a suction process, continuous adjustment of instantaneous high-power suction and continuous low-power current maintenance after in-place suction are implemented; and the PWM duty cycle is adjusted in real time during current shutdown to reduce mechanical impact.

The present disclosure provides a motion control method, applied by the preceding collimator apparatus. A stepper motor in the motor assembly directly drives a coupling in the motor assembly to rotate, the coupling is connected to the rotation seat assembly, the coupling absorbs eccentricity caused during movement, and the method includes: reading a planning sequence output by an upper computer software, and reading a preset collimator sequence; in a case where a plurality of preset collimators are loaded into the at least two assembly components in a one-to-one manner, determining whether a collimator at a position of a beam axis corresponds to the preset collimator sequence; in response to the collimator at the position of the beam axis corresponding to the preset collimator sequence, executing the planning sequence, and in response to the collimator at the position of the beam axis not corresponding to the preset collimator sequence, turning a collimator corresponding to a first preset position, a second preset position, or a third preset position to the position of the beam axis; and in a case where a collimator at a preset position is successfully turned to the position of the beam axis, sending an in-place signal, and in a case where the collimator at the preset position fails to be turned to the position of the beam axis, reporting a fault signal, where the beam axis is an axis of the beam hole;

determining whether execution of the planning sequence output by the upper computer software is completed, and in response to the execution of the planning sequence being completed, ending a current control; and in response to the execution of the planning sequence not being completed, returning to execute the operations of reading the planning sequence output by the upper computer software, reading the preset collimator sequence, and determining whether a current collimator at the position of the beam axis corresponds to the preset collimator sequence.

In an embodiment, a rotation seat of the rotation seat assembly is provided with a limit block, and after the stepper motor receives a command to drive the rotation seat to rotate, the limit block rotates along with the rotation seat to determine an initial position, where a positioning flow of the stepper motor includes: determining whether the stepper motor is in a ready state; in response to the stepper motor being in the ready state, performing a next operation; and in response to the stepper motor being not in the ready state, reporting a fault, and ending a current positioning flow; determining whether a current position is consistent with a preset position; in response to the current position being consistent with the preset position, ending a current positioning flow; and in response to the current position being inconsistent with the preset position, executing a next operation; rotating a position of the collimator to determine whether the collimator has been rotated to the preset position; in response to the collimator having been rotated to the preset position, a ready state of reaching the preset position according to a preset process is entered; and in response to the collimator not rotating to the preset position, controlling the stepper motor to rotate to allow the collimator to reach the preset position; in a case where the collimator times out and does not reach the preset position, reporting a fault; the electromagnetic pin being matched with the stepper motor to implement positioning, identification, and locking, and the electromagnetic pin being fixed to the rotation seat by the mounting ring and rotating with the rotation seat, where the electromagnetic pin includes N first micro switches, N is a natural number greater than or equal to three, and N is equal to a sum of a number of blind hole-collimators and a number of collimators, where N−1 first micro switches of the N first micro switches are fixed on the fixing seat, positions of the N−1 first micro switches correspond to N−1 collimators in a one-to-one manner, and the other one of the N first micro switches corresponds to the blind-hole collimator; the electromagnetic pin being a push-pull electromagnetic pin in a normally closed state; in a case where the electromagnetic pin is de-energized, the metal rod keeping a state of extending out of the electromagnetic pin; and in a case where the electromagnetic pin is energized, the metal rod retracting into the electromagnetic pin.

In an embodiment, a flow for implementing automatic positioning, identification, and locking of the electromagnetic pin includes: in a case where the motor assembly drives the rotation seat assembly to rotate, energizing the electromagnetic pin so that the metal rod retracts into the electromagnetic pin; in a case where the rotation seat assembly is rotated to a desired position, de-energizing the electromagnetic pin so that the metal rod extends out of the electromagnetic pin and is inserted into the tapered hole of the fixing seat, thereby blocking rotation of the rotation seat assembly; and when the metal rod of the electromagnetic pin is in contact with one of the N first micro switches at a corresponding position, triggering the one of the N first micro switches to detect whether the electromagnetic pin is locked in place to determine a station below the beam axis.

The present disclosure provides a motion control method, applied to the preceding collimator apparatus, includes: completing motor zero point initialization through a hard block and a limit switch detection mechanism, and performing motor initialization processing according to a grating reading fed back by the secondary position feedback mechanism and a theoretical value obtained by the primary position feedback mechanism; and implementing primary automatic motion, automatic positioning, and locking by the primary position feedback mechanism by means of an a-STEP closed loop, feeding back position information by the secondary position feedback mechanism in real time, and performing compensation motion and deviation correction by the primary position feedback mechanism according to the fed back position information to implement a two-stage closed-loop control.

In an embodiment, performing motor initialization processing according to the grating reading fed back by the secondary position feedback mechanism and the theoretical value obtained by the primary position feedback mechanism includes: using a grating position value of a preset position as a theoretical value of the preset position obtained by the primary position feedback mechanism, in a case where the stepper motor stops moving according to the theoretical value of the preset position, and a grating reading of a stop position of the stepper motor fed back by the secondary position feedback mechanism is consistent with the theoretical value of the preset position, using the theoretical value of the preset position as an initial theoretical value of the motor, and ending the motor initialization; and implementing primary automatic motion, automatic positioning, and locking by the primary position feedback mechanism by means of the a-STEP closed loop, feeding back the position information by the secondary position feedback mechanism in real time, and performing compensation motion and deviation correction by the primary position feedback mechanism according to the fed back position information to implement the two-stage closed-loop control includes: receiving, by the control circuit, a command sent by an upper computer and feeding back the command to the driver, sending, by the driver, a motion instruction to the stepper motor according to the command, making a push rod lock detection switch closed, powering on an electromagnetic push rod of the primary position feedback mechanism, reducing a coil current to 10% of a rated value, and pulling the electromagnetic push rod out of the fixing seat, where the driver is an a-STEP driver; implementing angular resolution and motor output torque by the stepper motor at a deceleration ratio of 100:1 to implement primary motion positioning; and feeding back data of a subdivided rotation encoder built into the stepper motor to a driving front stage through a decelerator and a transmission mechanism to implement a first-stage closed-loop control, where the stepper motor is an a-STEP stepper motor; after the collimator moves in place, turning off the push rod lock detection switch, adjusting a pulse width modulation (PWM) duty cycle by the control circuit, the electromagnetic push rod moving to the fixing seat to implement primary positioning and locking, and returning motion information by the control circuit to the driver; reading a grating position by the reading head in real time, and determining a read grating reading and a range of a theoretical position Δ; calculating, by the control circuit, a motion direction of the motor and a number of steps of the motor according to a current position of the collimator and a station position where the collimator needs to move, and sending a motion instruction to the stepper motor; and in a case where a difference between the grating reading and a target constant deviates from the range of the theoretical position Δ, sending a correction command to the stepper motor and the driver by the control circuit to move the collimator to the station position where the collimator needs to move, and correcting angle deviation, so as to implement a second-stage closed-loop control; and after the stepper motor receives the motion command, repeatedly executing operations from the first-stage closed-loop control to the second-stage closed-loop control until the rotation seat assembly stops moving, and after the rotation seat assembly stops moving, the difference between the grating reading and the target constant being in the range of the theoretical position Δ, and the electromagnetic push rod being locked in a hole and triggering a micro switch to return an in-place signal to the upper computer.

In an embodiment, the rotation seat assembly has two forward and reverse rotation over-range limit points, and completing the motor zero point initialization includes: detecting, by the control circuit, a relative position of the rotation seat assembly to the fixing seat by using a micro switch, setting a reverse rotation over-range limit point of the rotation seat assembly as a positioning origin, and searching for the positioning origin by using a press-contact mode: controlling the rotation seat assembly to rotate reversely by the control circuit, determining a grating reading of an end face of the rotation seat assembly and a motor encoder reading to find the positioning origin, and rotating the rotation seat assembly forward after the positioning origin is determined, to allow all stations of the at least two collimators sequentially pass through the beam hole.

In an embodiment, using the grating position value of the preset position as the theoretical value of the preset position obtained by the primary position feedback mechanism includes: obtaining, by the control circuit, a motor stop bit END, and determining, whether the motor stop bit END is equal to 1; in response to the motor stop bit END being equal to 1, giving no alarm; and in response to the motor stop bit END being not equal to 1, stopping operation of the stepper motor and feeding back alarm information; and in a case of no alarm, refreshing, by the control circuit, the grating reading of the stop position of the stepper motor, writing the grating reading as departure data into a register, automatically updating, by the stepper motor, the grating position value of the preset position according to the departure data, and using the grating position value of the preset position as the theoretical value of the preset position; and in a case of giving the alarm, refreshing, by the control circuit, local alarm information with fed back alarm information, controlling and displaying the fed back alarm information, and reporting a data packet for processing, wherein the preset position includes a plurality of stations; in the case where the stepper motor stops moving according to the theoretical value of the preset position, and the grating reading of the stop position of the stepper motor fed back by the secondary position feedback mechanism is consistent with the theoretical value of the preset position, using the theoretical value of the preset position as the initial theoretical value of the motor includes: after the stepper motor executes a motion command to operate to each of the plurality of stations, verifying conformity between a grating reading of a stop position of the stepper motor and a theoretical value of the each of the plurality of stations, wherein the conformity includes a comparison of a difference between the grating reading and the theoretical value with a preset difference range, and the motion command includes the theoretical value of the each of the plurality of stations; and in response to the difference between the grating reading and the theoretical value being in the preset difference range, saving the grating reading as a position parameter of the each of the plurality of stations, and ending the motor initialization; and in response to the difference between the grating reading and the theoretical value not being in the preset difference range, executing initialization error reporting, setting an initialization failure mark, and ending the motor initialization.

DETAILED DESCRIPTION

The present disclosure is described with reference to drawings and embodiments.

Figure 1:
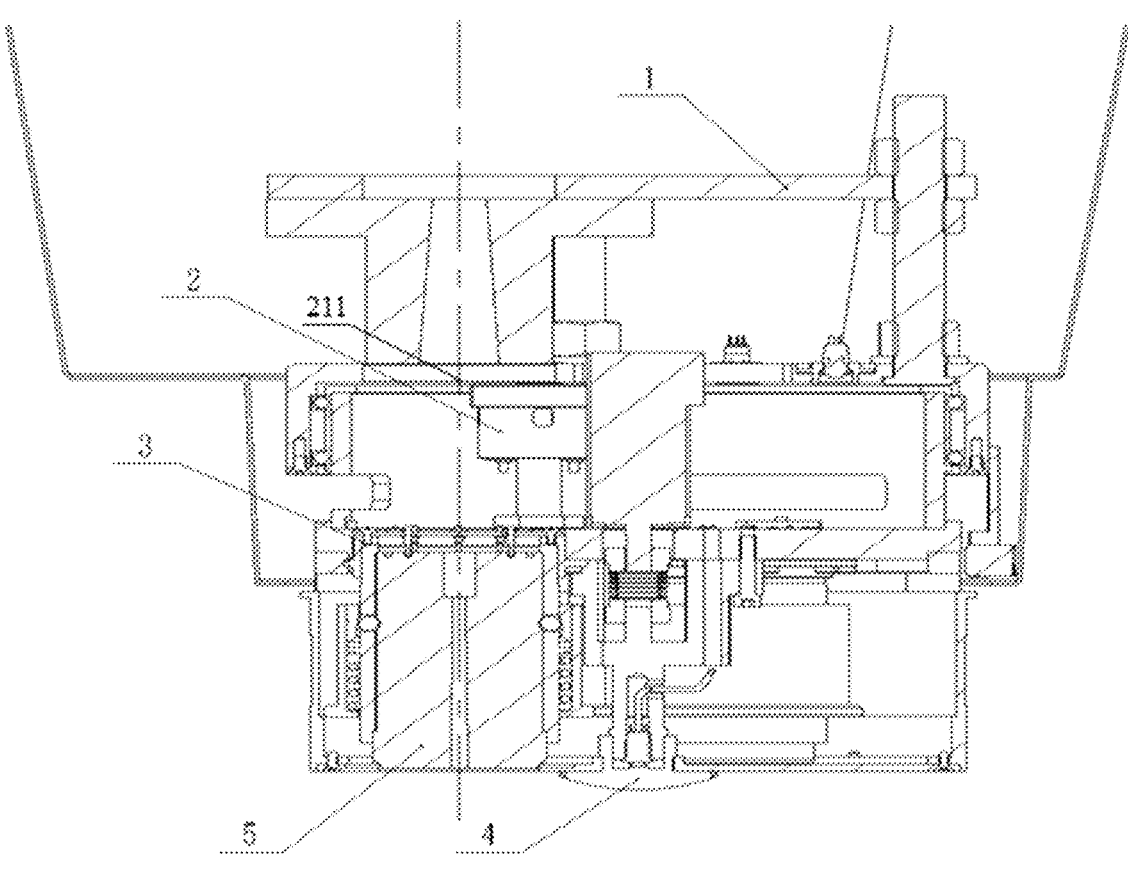
FIG. 1 is a general assembly view of a collimator apparatus capable of implementing automatic and quick switching according to an embodiment of the present disclosure.
Figure 4:
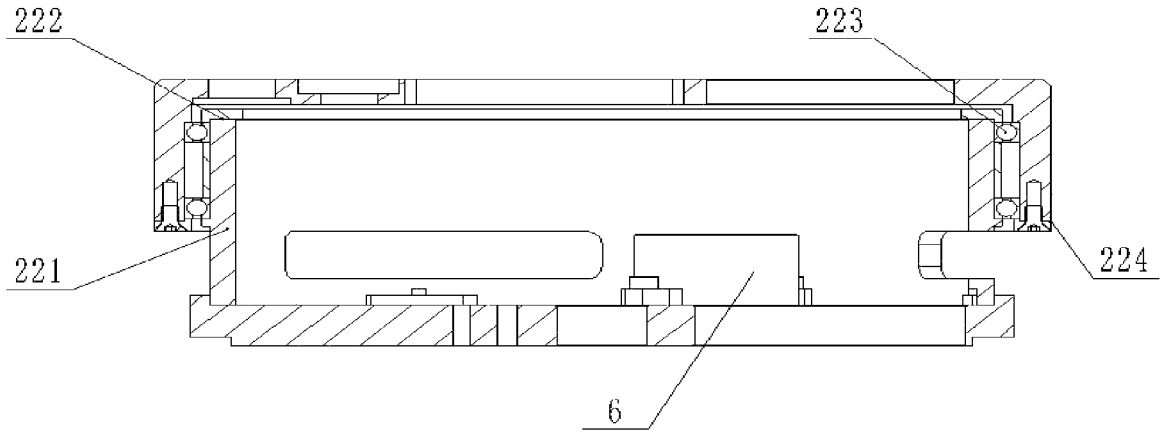
FIG. 4 is a structure view of a rotation seat assembly according to an embodiment of the present disclosure.

As shown in FIG. 1 and FIG. 4, the present disclosure provides a collimator apparatus capable of implementing automatic and quick switching. The collimator apparatus includes an adjustment frame assembly 1, a transmission assembly 2, an assembly component 3, a protection disk assembly 4, a collimator 5, and a blind-hole collimator 6. The adjustment frame assembly 1 is located above the transmission assembly 2. The transmission assembly 2 is connected to a primary collimator by three sets of screws and nuts. The assembly component 3 is located below the transmission assembly 2 and is fixed to a rotation seat assembly on the transmission assembly 2. The rotation seat assembly drives the assembly component 3 through a motor assembly to move. The collimator 5 is located and locked in the assembly component 3.

Figure 2:
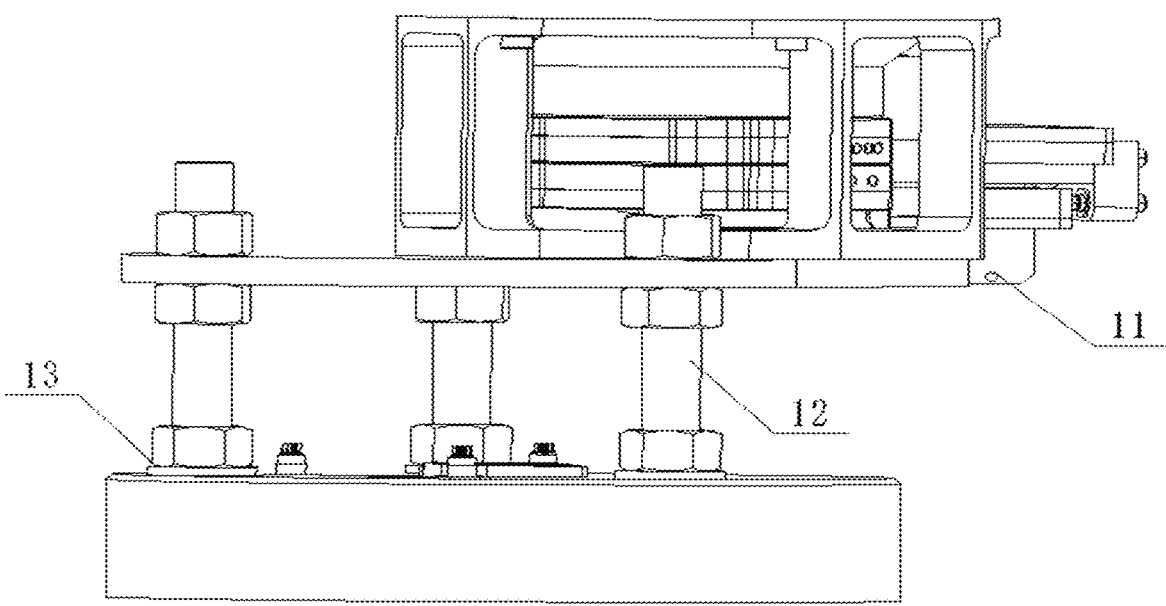
FIG. 2 is a structure view of an adjustment frame assembly according to an embodiment of the present disclosure.

As shown in FIG. 2, the adjustment frame assembly 1 includes a connection plate 11, a screw 12, and a nut 13. A secondary collimator support structure (i.e., the structure of the collimator apparatus excluding the adjustment frame assembly 1 provided in embodiments of the present disclosure) is fixed to the end of a primary collimator apparatus by the connection plate 11 in the adjustment frame assembly 1. The distance from a secondary collimator (i.e., the collimator 5) to a target point can be adjusted by adjusting the screw 12 and the nut 13. Three sets of screws 12 and nuts 13 are provided.

Figure 3:
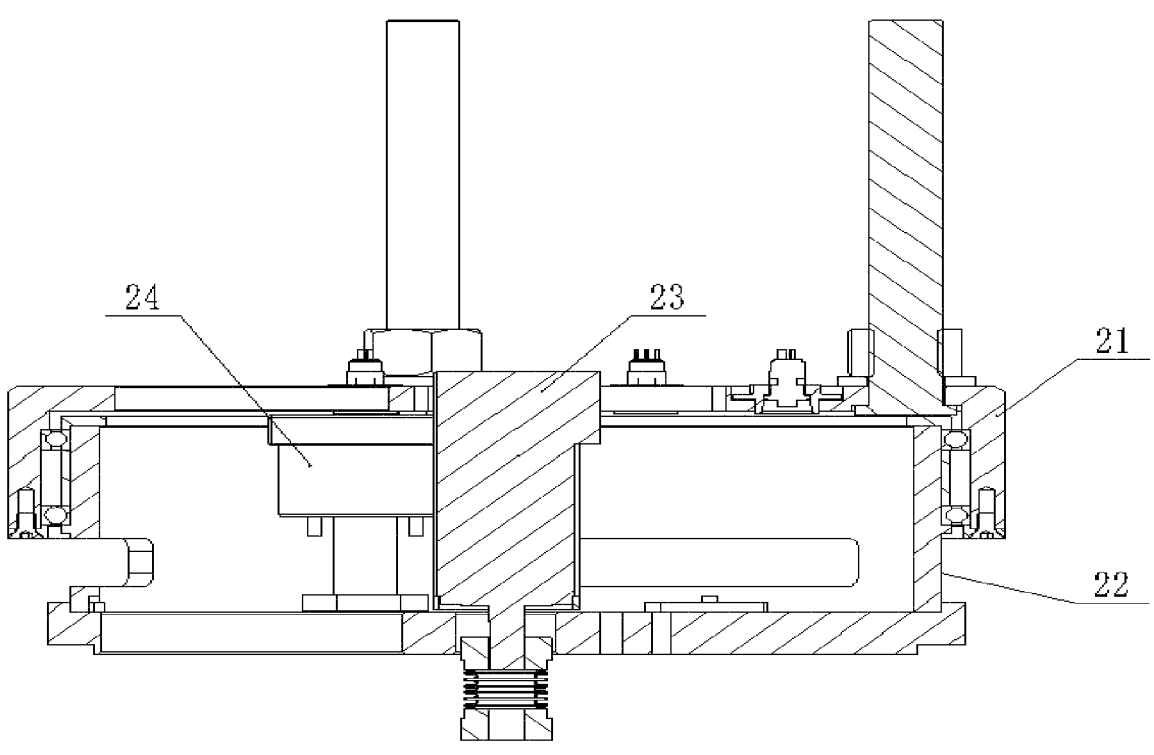
FIG. 3 is a structure view of a transmission assembly according to an embodiment of the present disclosure.

As shown in FIG. 1 and FIG. 3, the transmission assembly 2 includes a fixing seat 21, a rotation seat assembly 22, a motor assembly 23, and an electromagnetic pin assembly 24. The fixing seat 21 is provided with a beam hole 211. The motor assembly 23 drives the rotation seat assembly 22 to rotate a designated collimator 5 below the beam hole 211, thereby implementing automatic and quick switching of multiple stations of the collimator 5.

As shown in FIG. 4, the rotation seat assembly 22 includes a rotation seat 221, a bearing inner race end cap 222, a thin-wall bearing 223, and a bearing outer race end cap 224.

Two thin-wall bearings 223 are mounted between the rotation seat 221 and the fixing seat 21. The rotation seat 221 is rotated under the action of the motor assembly 23 through thin-wall bearings. A thin-wall bearing 223 has a large inner diameter (greater than 180 mm), a small cross-sectional size, and a light weight to bear axial and radial forces. The rotation speed is generally about 3000 rpm. To make a collimator system work smoothly, two bearings are mounted in pairs, which helps to ensure uniform force and smooth rotation of the overall collimator during operation. Under a vertical operating condition, the weight of the collimator system is borne by two thin-wall bearings 223 subjected to axial forces, and under a horizontal operating condition, the weight of the collimator system is borne by two thin-wall bearings 223 subjected to radial forces.

Outer walls of the two thin-wall bearings 223 are provided with two bearing end caps. The two bearing end caps include a bearing outer race end cap 224 and a bearing inner race end cap 222 to fix the bearings. The gravity of the collimator is transmitted from the balls to the bottom. When the secondary collimator (collimator 5) is placed downward, the bearing outer race end cap 224 bears the gravity and plays a load-bearing role. If the secondary collimator (collimator 5) is rotated to be placed upwards, the bearing inner race end cap 222 plays a load-bearing role.

A blind-hole collimator 6 and three circular holes are disposed on the rotation seat assembly 22. The blind-hole collimator 6 is mounted on the rotation seat 221. In a non-treatment state, the blind-hole collimator 6 is rotated to a position below the beam hole 211 so that a dark current can be prevented from damaging a patient.

The three circular holes are evenly distributed at 120°. The blind-hole collimator 6 is located in the middle of two circular holes. The blind-hole collimator 6 is made of tungsten nickel copper alloy or tungsten nickel iron alloy. Three circular holes are configured for fixed connection of the assembly component 3.

Figure 5:
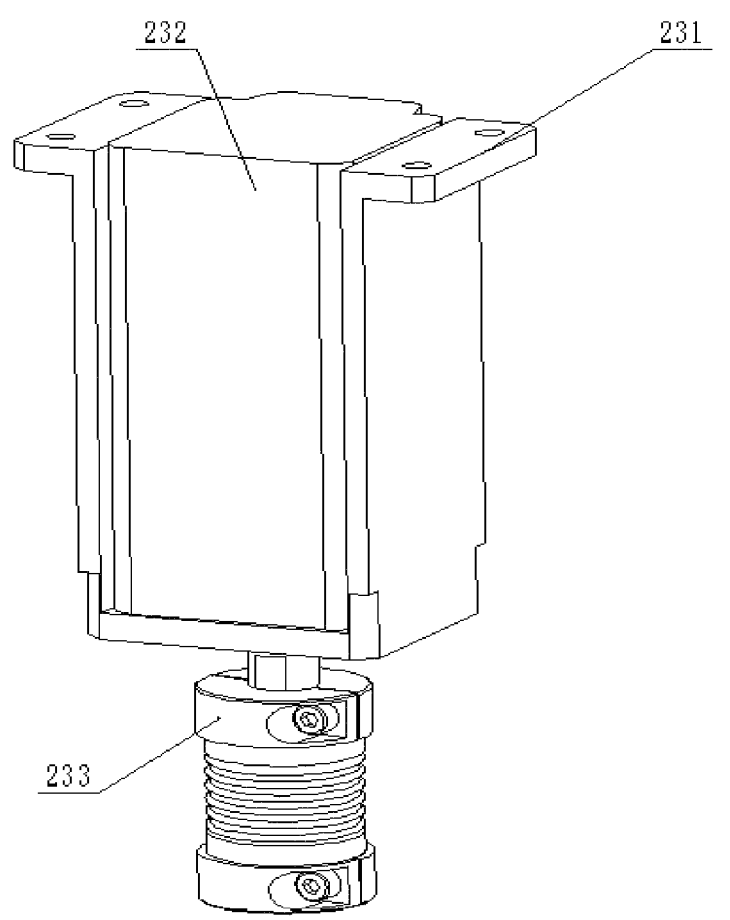
FIG. 5 is a structure view of a motor assembly according to an embodiment of the present disclosure.

As shown in FIG. 5, the motor assembly includes a motor bracket 231, a stepper motor 232, and a coupling 233. The stepper motor 232 is fixed to the fixing seat 21 by the motor bracket 231. When the collimator 5 with a certain aperture is selected according to a treatment plan, the output shaft of the stepper motor 232 drives the rotation seat 221 through the coupling 233 to rotate. In this embodiment, three collimators 5 are mounted on the rotation seat 221. A desired collimator 5 can be rotated below the center of the beam hole 211. In the rotation process, the coupling 233 can absorb eccentricity caused during movement.

The motor assembly 23 adopts a direct transmission manner. The stepper motor 232 is used to directly drive a shaft to rotate. The maximum output torque is 2.4 N/m. A decelerator with a deceleration ratio of 1:100 is disposed in the motor assembly 23. In this manner, the number of transmission stages can be reduced, and the transmission accuracy and efficiency can be improved. The structure is compact and meets space limitation requirements. The coupling 233 is a flexible coupling.

Figure 11:
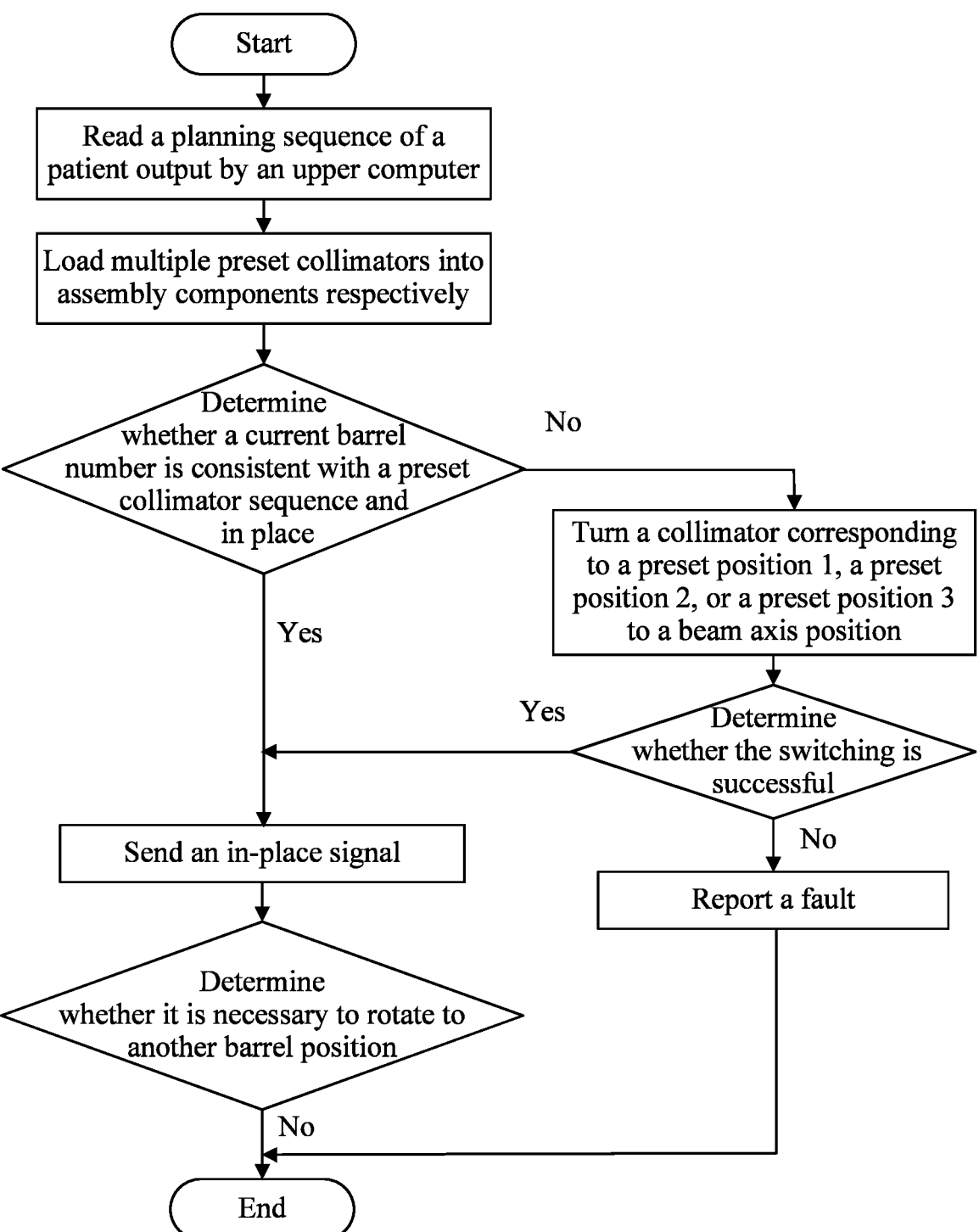
FIG. 11 is a flowchart of a motion control method according to an embodiment of the present disclosure.
Figure 13:
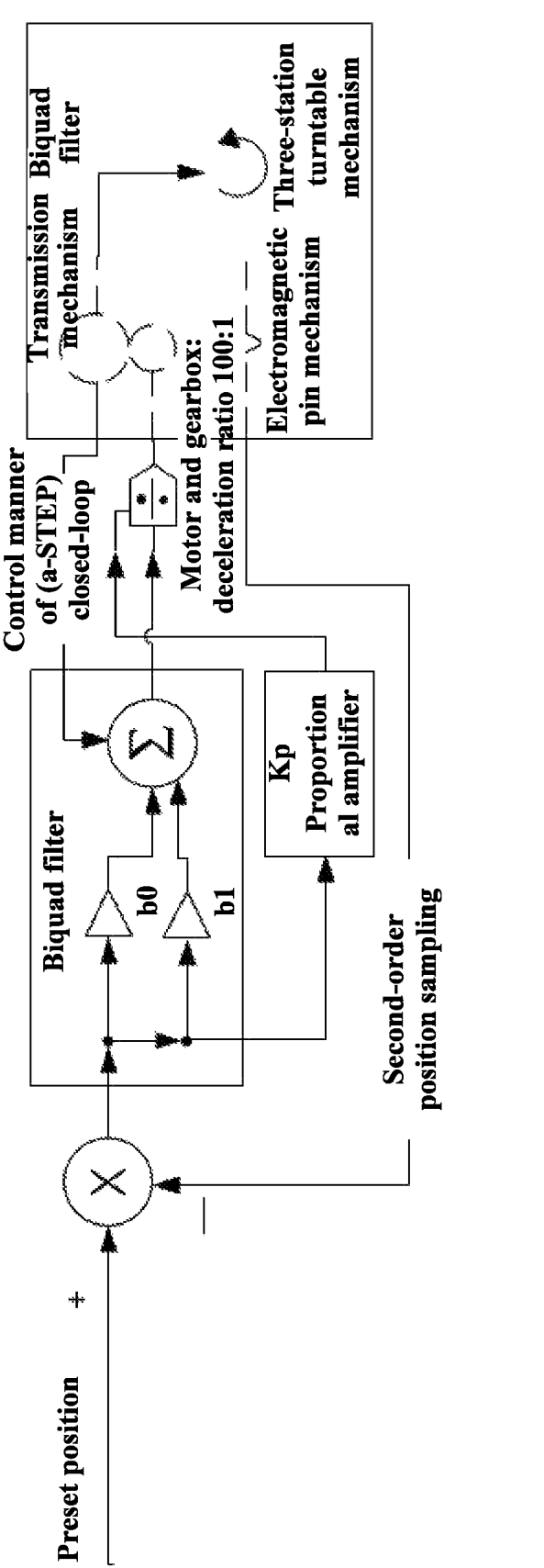
FIG. 13 is a flowchart of another motion control method according to an embodiment of the present disclosure.
Figure 14:
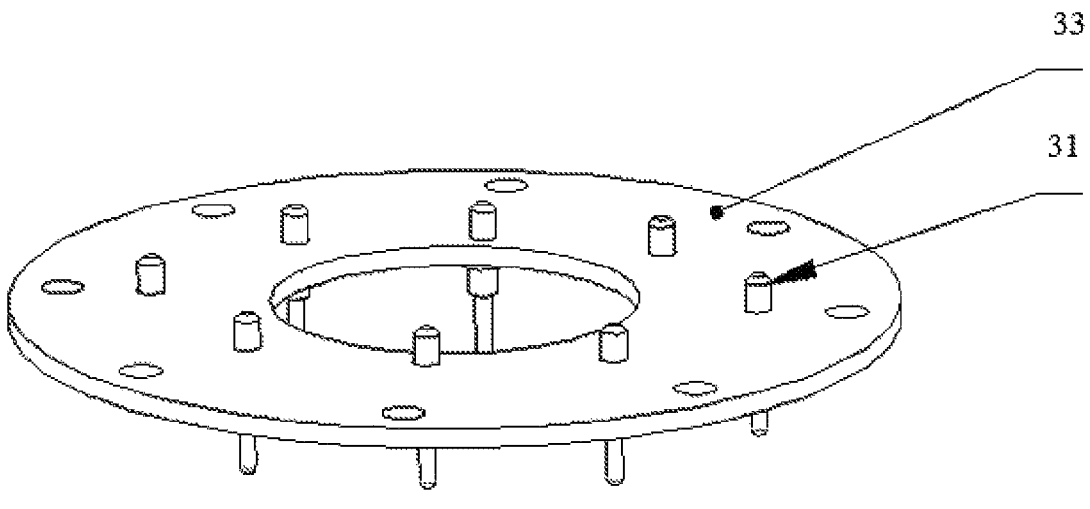
FIG. 14 is a diagram showing insertion of a groove identification PCB probe assembly according to an embodiment of the present disclosure.
Figure 15:
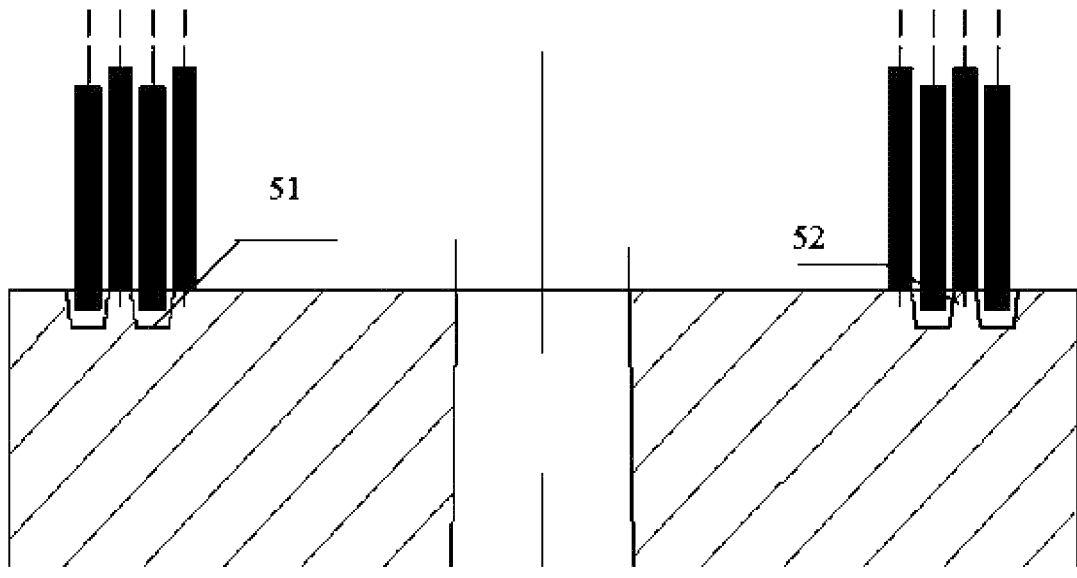
FIG. 15 is a schematic diagram showing insertion of a groove physical code according to an embodiment of the present disclosure.

In the present disclosure, the stepper motor 232 is a one-stage automatic positioning, identification, and locking apparatus. The apparatus converts an electric pulse into an angular displacement, and controls the angular displacement by controlling the number of pulses to achieve the purpose of accurate positioning. There is no accumulated error, and the repeated positioning accuracy is high. Thus, the positioning accuracy requirements can be met. As shown in FIGS. 11 and 13, an operation flow is as follows.

In step 1, an upper computer software outputs a planning sequence.

In step 2, the output planning sequence is read, and a preset collimator sequence is read.

In step 3, multiple preset collimators are loaded into assembly components respectively.

In step 4, an identification assembly is used to determine whether a collimator at a current beam axis position corresponds to the preset collimator sequence. If the collimator at the current beam axis position corresponds to the preset collimator sequence, an output plan is executed. If it is determined that the collimator at the current beam axis position does not correspond to the preset collimator sequence, a collimator corresponding to a preset position 1, a preset position 2, or a preset position 3 needs to be turned to the beam axis position. If a collimator is successfully turned to the beam axis position, an in-place signal is sent. If the collimator fails to be turned to the beam axis position, a fault signal is reported.

In step 5, it is determined whether the execution of the output plan sequence is completed. If the execution of the plan sequence is completed, the process ends.

In step 6, if the execution of the output plan sequence is not completed, the process proceeds to step 2.

The collimator in the beam axis direction can be turned from collimator No. 1 to collimator No. 2 or No. 3 through automatic rotation.

As shown in FIG. 13, a detailed flowchart of an accurate motion control method is as follows.

1. Angular ultra-high resolution and sufficient motor output torque are implemented at an ultra-high deceleration ratio of 100:1.

2. Primary positioning is implemented by relying on an a-STEP closed loop: data of a subdivided rotation encoder built into a motor is fed back to a driving front stage through a decelerator and a transmission mechanism to implement a first-stage closed loop of the position.

3. A biquad filtering algorithm is inserted into a first-stage closed-loop network, effectively eliminating subdivision clearance and transmission jitter and ensuring smooth positioning of the motor.

4. The second-order position sampling of an electromagnetic pin is differentially fed. Then, the gain of a second-order closed loop is programmatically adjusted through a biquad filter closed-loop network and a proportional amplifier to implement second-stage accurate positioning.

Figure 12:
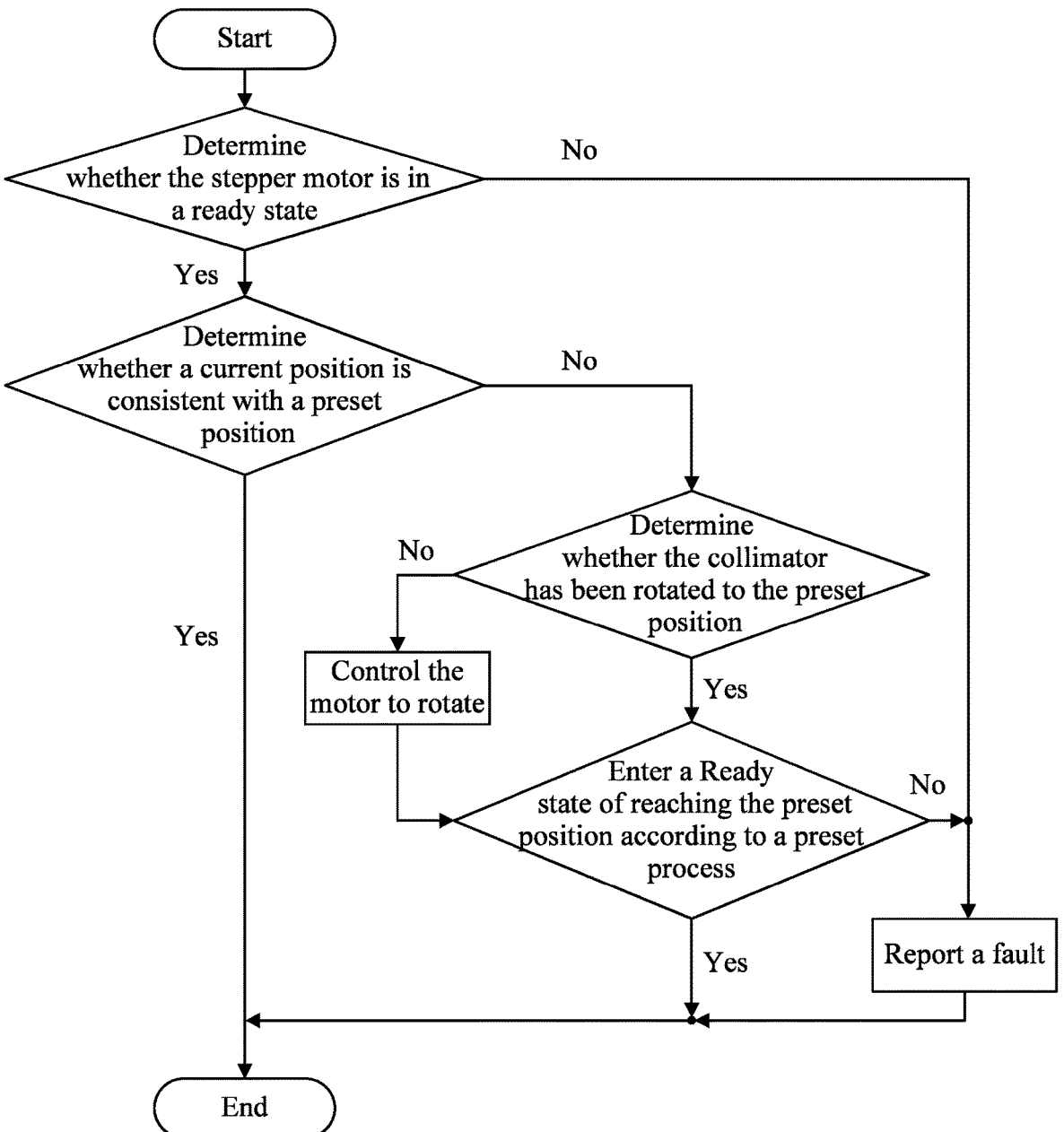
FIG. 12 is a flowchart of a stepper motor positioning method according to an embodiment of the present disclosure.

As shown in FIG. 12, the positioning flow of the stepper motor is as follows.

In step 1, it is determined that whether the stepper motor is in a ready state. If it is determined that the stepper motor is in the ready state, the following steps are performed. If it is determined that the stepper motor is not in the ready state, a fault is reported, and the process ends.

In step 2, it is determined that whether a current position is consistent with a preset position. If the current position is consistent with the preset position, the process ends. If the current position is inconsistent with the preset position, the following steps are executed.

In step 3, the position of a collimator is rotated, and it is determined whether the collimator has been rotated to the preset position. If the collimator has been rotated to the preset position, a ready state of reaching the preset position according to the preset process is entered. If the collimator is not rotated to the preset position, the motor is controlled to rotate to allow the collimator to reach the preset position.

In step 4, if the collimator times out and does not reach the preset position, a fault is reported.

Figure 6:
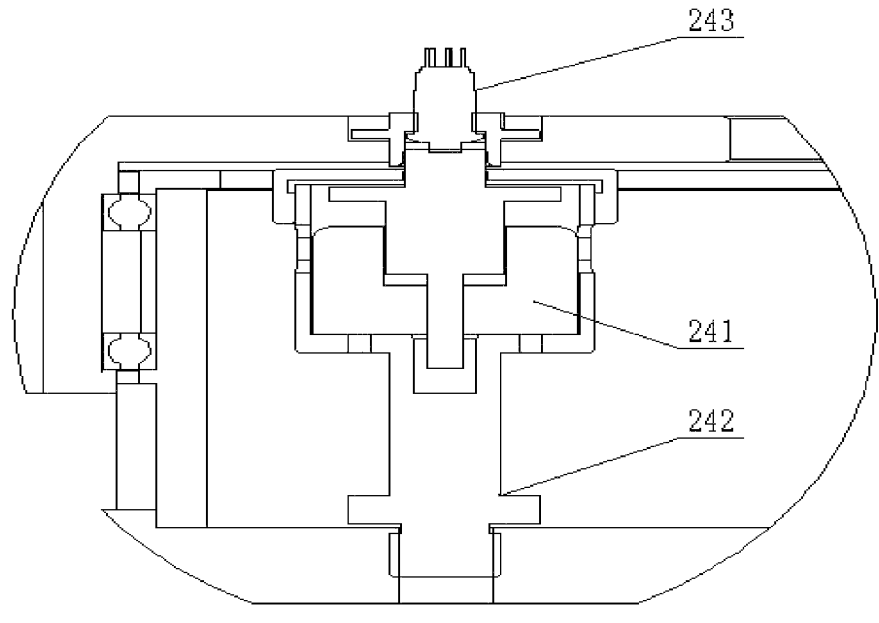
FIG. 6 is a structure view of an electromagnetic pin assembly according to an embodiment of the present disclosure.
Figure 7:
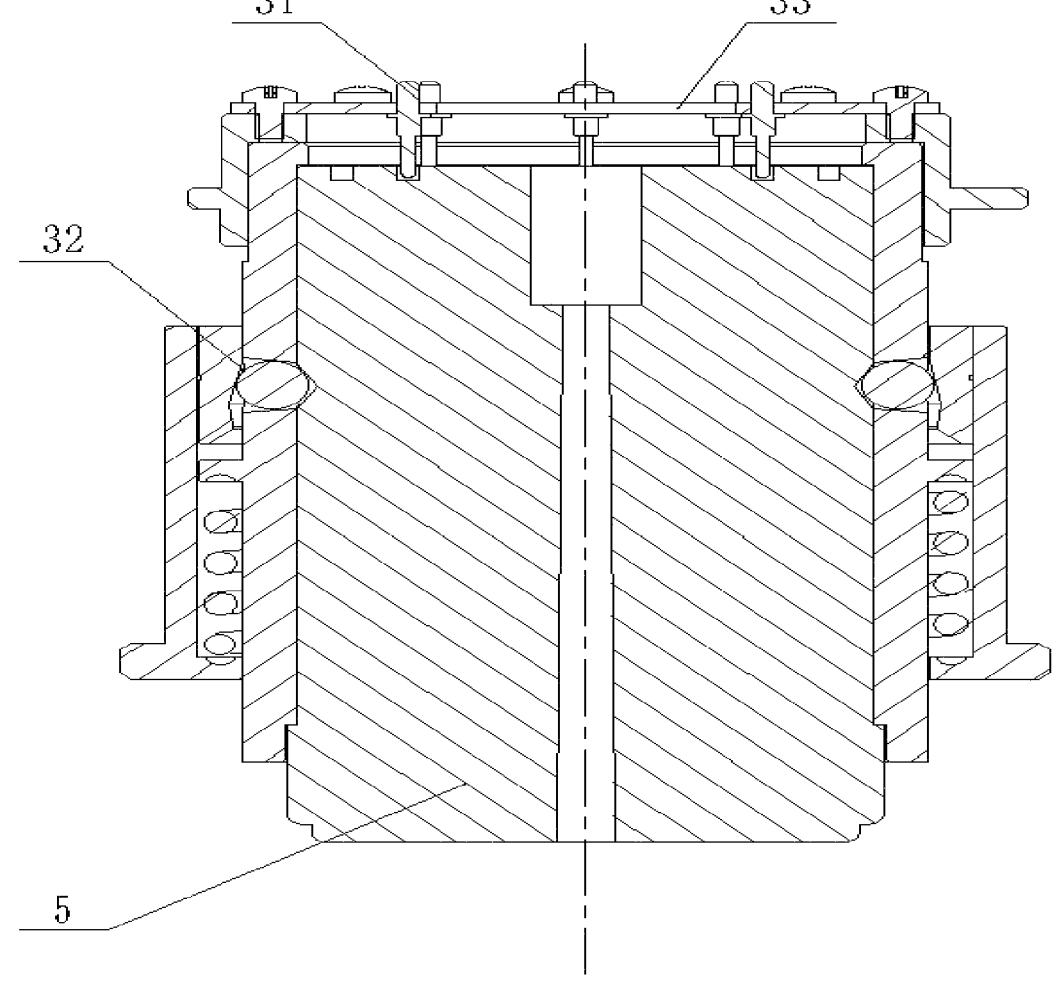
FIG. 7 is a structure view of an assembly component according to an embodiment of the present disclosure.

As shown in FIG. 6, the electromagnetic pin assembly 24 includes an electromagnetic pin 241, a mounting ring 242, and a first micro switch 243. The electromagnetic pin 241 is fixed to the rotation seat 221 by the mounting ring 242 and rotates with the rotation seat 221. In this embodiment, the electromagnetic pin assembly 24 includes four first micro switches 243. Three first micro switches 243 are fixed to the fixing seat 21 and circumferentially distributed with intervals of 120°. Positions of the three first micro switches correspond to three collimators 5 respectively. The other one first micro switch 243 corresponds to the blind-hole collimator 6.

The electromagnetic pin 241 is a push-pull electromagnetic pin in a normally closed state. When the electromagnetic pin 241 is de-energized, a metal rod of the electromagnetic pin 241 keeps a state of extending out of the electromagnetic pin 241. When the electromagnetic pin 241 is energized, the metal rod retracts into the electromagnetic pin 241. The electromagnetic pin assembly 24 can implement automatic positioning, identification, and lock of the rotation seat assembly 22. When the motor assembly 23 drives the rotation seat 221 to rotate, the electromagnetic pin 241 is energized, and the metal rod retracts into the electromagnetic pin 241. When the rotation seat 221 is rotated to a desired position, the electromagnetic pin 241 is de-energized, and the metal rod extends out of the electromagnetic pin 241 and is inserted into the tapered hole of the fixing seat 21 so that the rotation seat 221 cannot be rotated. The metal rod contacts with a first micro switch 243 at a corresponding position, and the first micro switch 243 is triggered to send an electrical signal. Thus, a system knows a type of a collimator below the center of the beam hole 211.

As shown in FIGS. 7 to 9 and 14 to 15, the assembly component 3 includes a collimator identification assembly composed of a spring probe 31 and an annular PCB board 33, and a locking assembly 32.

The collimator identification adopts a groove physical code manner. A concave portion 51 or a convex portion 52 is disposed at a corresponding position on the top surface of a collimator 5. The probe 31 with a telescoping spring is disposed above the collimator 5, corresponds to the concave portion or the convex portion, and detects a corresponding electrical signal. When a concave portion is located below the probe 31, the probe 31 has no electrical contact with a secondary collimator (i.e., the collimator 5), so that no current passes through the probe 31, and a voltage signal is "1". When a convex portion is located below the probe 31, the probe 31 is in contact with the secondary collimator (i.e., the collimator 5), so that a current passes through the probe 31, and a voltage signal is "0".

At different radii of the top surface of the collimator 5, concave portions and convex portions with a total number of 4 are machined. The concave portions and convex portions are identified to form a set of 4 bit binary code corresponding to one of 16 collimator types. Different types of collimators 5 use different codes. The probe 31 is disposed on the PCB board. A code identification circuit identifies a type of the collimator through a code composed of voltage signals.

Figure 8:
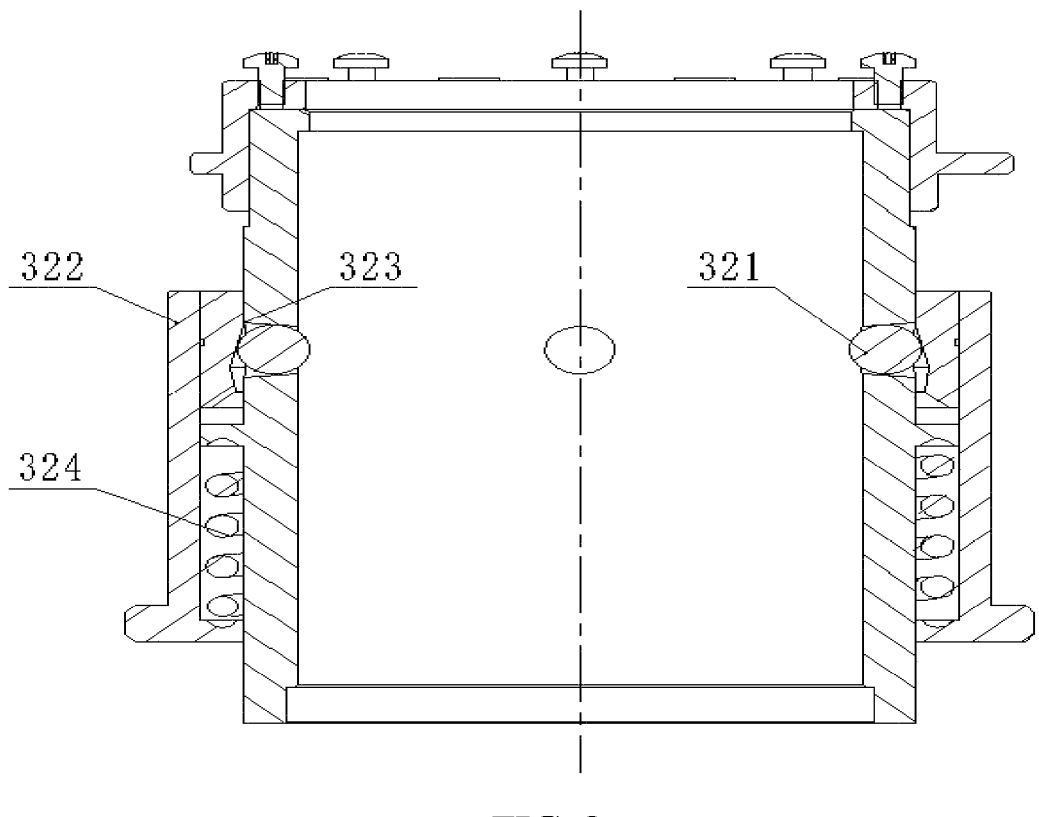
FIG. 8 is a structure view of a locking assembly according to an embodiment of the present disclosure.
Figure 9:
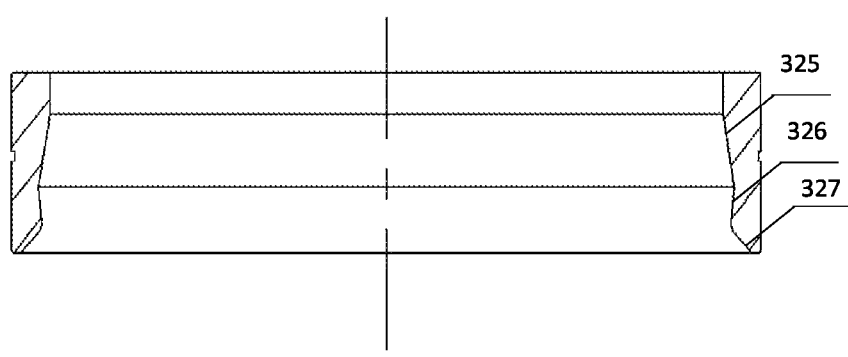
FIG. 9 is a structure view of a tapered sleeve according to an embodiment of the present disclosure.

As shown in FIG. 8 and FIG. 9, the locking assembly 32 fixes the collimator 5 in a ball locking manner. The locking assembly 32 includes a ball 321, an outer sleeve 322, an inner tapered sleeve 323, and a spring 324. The outer sleeve 322 is fixed to the inner tapered sleeve 323. The inner tapered sleeve 323 is in contact with the ball 321. The ball 321 is in contact with the ball groove of the collimator 5. The spring 324 is disposed below the inner tapered sleeve 323 and is connected to the inner tapered sleeve 323.

The inner tapered sleeve 323 is provided with three tapered surface portions which are a first tapered surface 325, a second tapered surface 326, and a third tapered surface 327. In a portion where the first tapered surface 325 is disposed, the cross-sectional area of the inner tapered sleeve 323 gradually decreases from up to down. In a portion where the second tapered surface 326 is disposed, the cross-sectional area of the inner tapered sleeve 323 gradually increases from up to down. In a portion where the third tapered surface 327 is disposed, the cross-sectional area of the inner tapered sleeve 323 gradually decreases from up to down.

The first tapered surface 325 is tangential to the ball 321 when the first tapered surface 325 is in contact with the ball 321. The second tapered surface 326 is tangential to the ball 321 when the second tapered surface 326 is in contact with the ball 321. The ball 321 is tangential to two tapered angles of the ball groove of the collimator 5.

Three-stage lock protection exists. A first-stage mechanical locking manner is to perform automatic locking through the ball 321. When the spring 324 is in a normal work state, the spring 324 applies a pressure to the inner tapered sleeve 323 to ensure effective contact of the ball 321 with the first tapered surface 325 of the inner tapered sleeve 323 and make the first tapered surface 325 press the ball 321 to lock the collimator. A second-stage mechanical locking manner is that when the spring 324 fails and loses a pulling force to the inner tapered sleeve 323, the outer sleeve 322 and the inner tapered sleeve 323 move upward, and the ball 321 no longer presses the collimator 5. The collimator 5 moves downward for a certain distance until the second tapered surface 326 of the inner tapered sleeve 323 re-presses the outermost ball 321. The ball 321 re-presses the ball groove of the collimator 5 to implement the second-stage mechanical locking of the collimator to ensure that the collimator 5 does not fall off. In the locking manner of the present disclosure, when the spring 324 is in the normal work state, the first tapered surface presses the ball 321 so that the ball 321 presses the groove of the collimator 5 and locks the collimator 5. A resistor on the collimator 5 compresses the probe 31 on the circuit board so that the specification type of the collimator 5 can be detected. The tapered sleeve with three tapered surfaces and the ball 321 may cooperate with each other to achieve the protective function during both normal and failure of the spring 324

The assembly locked with the ball 321 is axisymmetric.

The outer sleeve 322 and the inner tapered sleeve 323 are fixed by a set screw. The outer sleeve 322 and the inner tapered sleeve 323 move at the same time when moving. The inner tapered sleeve 323 is made of brass because of the need to press the ball 321 and the high hardness requirement. Considering that the apparatus should be as light as possible, the outer sleeve 323 is made of aluminum alloy which is small in density and light in weight. The ball 321 is a quenched steel ball.

The collimator apparatus also includes a position sensor. The position sensor is disposed at a distance from a metal sheet on the outer sleeve 322. A one-stage locking check protection manner is that when the collimator 5 is locked, the outer sleeve 322 is pulled downward so that the metal sheet on the outer sleeve 322 approaches the position sensor. When the distance between the metal sheet on the outer sleeve 322 and the position sensor is less than 2 mm, the sheet metal on the outer sleeve 322 is detected by the position sensor. Thus, it can be ensured that the secondary collimator (i.e., the collimator 5) is mounted and locked in place, thereby ensuring the safety and reliability.

A mounting and locking manner of a collimator is that a collimator 5 is mounted in a rotation seat 221, the outer sleeve 322 is pulled downward by hand to make the inner tapered sleeve 323 press the ball 321 so that the ball 321 presses the groove of the collimator 5 and locks the collimator 5. When the collimator 5 is to be replaced, the collimator 5 is held by hand first, and then the outer sleeve 322 is pushed upwards to make the ball 321 move to release the locking state so that the collimator 5 can slide down.

Figure 10:
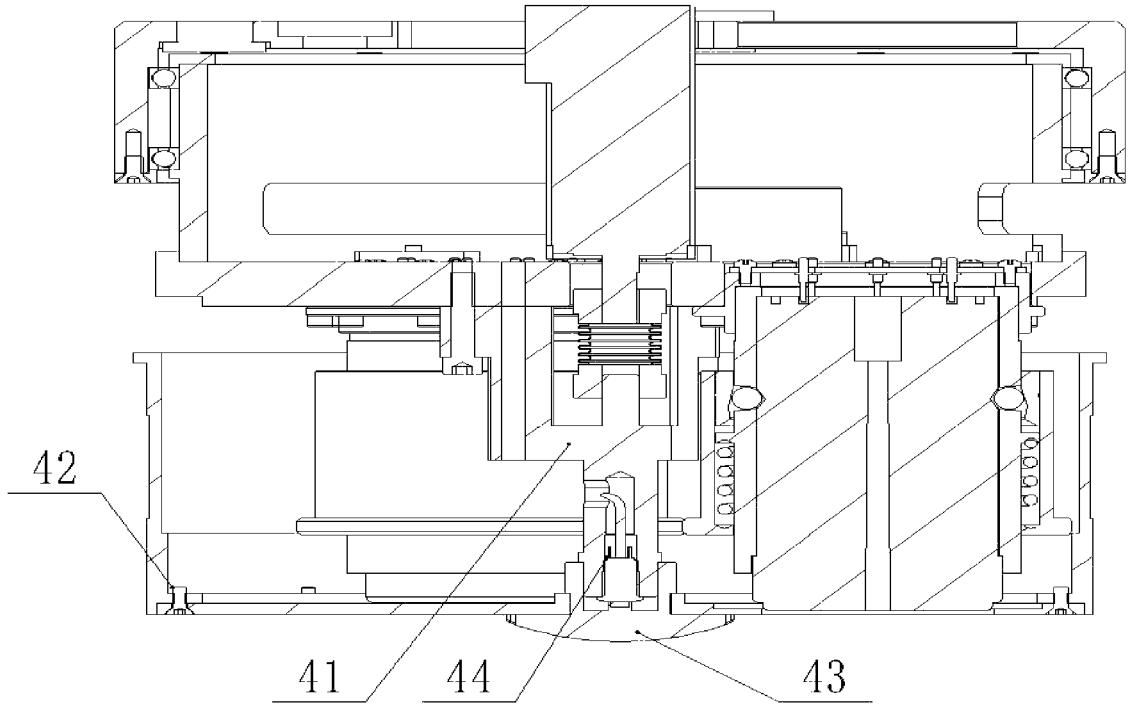
FIG. 10 is a structure view of a protection disk assembly according to an embodiment of the present disclosure.

As shown in FIG. 10, a protection disk assembly 4 includes a protection disk mounting rod 41, a protection disk 42, a protection disk rotation nut 43, and a second micro switch 44. There is a clearance between the protection disk 42 and the bottom of the collimator 5. A three-stage protection apparatus is designed at the bottom of the collimator 5. Once a spring 324 in a locking assembly 32 of a single collimator 5 fails, the three-stage protection apparatus can protect the collimator 5 when the collimator 5 falls off.

After three collimators 5 are locked by springs and balls, the protection disk 42 is mounted at the bottom. Then, the protection disk rotation nut 43 is mounted. The second micro switch 44 is mounted in the protection disk mounting rod 41.

When the protection disk rotation nut 43 is tightened, the protection disk rotation nut 43 presses the second micro switch 44. In this manner, whether the protection disk rotation nut 43 is mounted in place can be detected. Three through holes are formed in the protection disk mounting rod 41 to allow wires of resistance identification apparatuses of collimators 5 to pass through the through holes. The wire of the second micro switch 44 also needs to pass through an intermediate hole to ensure that wires are neat and easy to maintain.

On the basis of a conventional collimator, the collimator 5 in the present disclosure is provided with a groove and a ball groove. The collimator 5 is made of tungsten nickel copper alloy or tungsten nickel iron alloy and has a tapered aperture. The angle of the ball groove is tangential to the ball configured for locking.

In the preceding embodiments, at least two collimators are mounted on a treatment head at the same time. During a treatment process, the treatment head can quickly switch collimators according to a treatment plan. In most cases, a collimator can be replaced without stopping the treatment. In this manner, an automatic and quick switching collimation system is implemented, and treatment time is saved. In the treatment process of the collimation system, a secondary collimator moving accurately and quickly to a designated station is the key step. However, due to the influence of the weight of a loaded collimator during the movement of the treatment, some parts may be deformed. Especially when the collimator is in different postures due to robot motion, different loads can easily lead to position deviation, and the secondary collimator are not directly driven to rotate at the same angle. As a result, the patient plane accuracy obtained by accumulating multiple factors has a large deviation, influencing the treatment effect. However, complete coincidence of the beam axis of the secondary collimator and the beam axis of a primary collimator cannot be ensured by merely relying on motor motion positioning and locking, leading to treatment beam deformity and affecting the treatment effect.

To solve the preceding technical problems, embodiments of the present disclosure provide an automatic and quick switching collimator apparatus for implementing accurate motion control. Multiple secondary collimators with different apertures are mounted on a rotation seat assembly in an accelerator head. Automatic rotation, automatic identification, and automatic locking of the rotation seat assembly are implemented through a primary position feedback mechanism. Position deviation of the primary position feedback mechanism is fed back and corrected in real time through a secondary position feedback mechanism. When the multiple collimators with different apertures mounted on the rotation seat assembly are automatically and rapidly replaced in one treatment fraction, position information is fed back in real time, and closed-loop communication of accurate motion control and accurate motion control of different collimators are implemented. The automatic and quick switching saves the treatment time.

Figure 16:
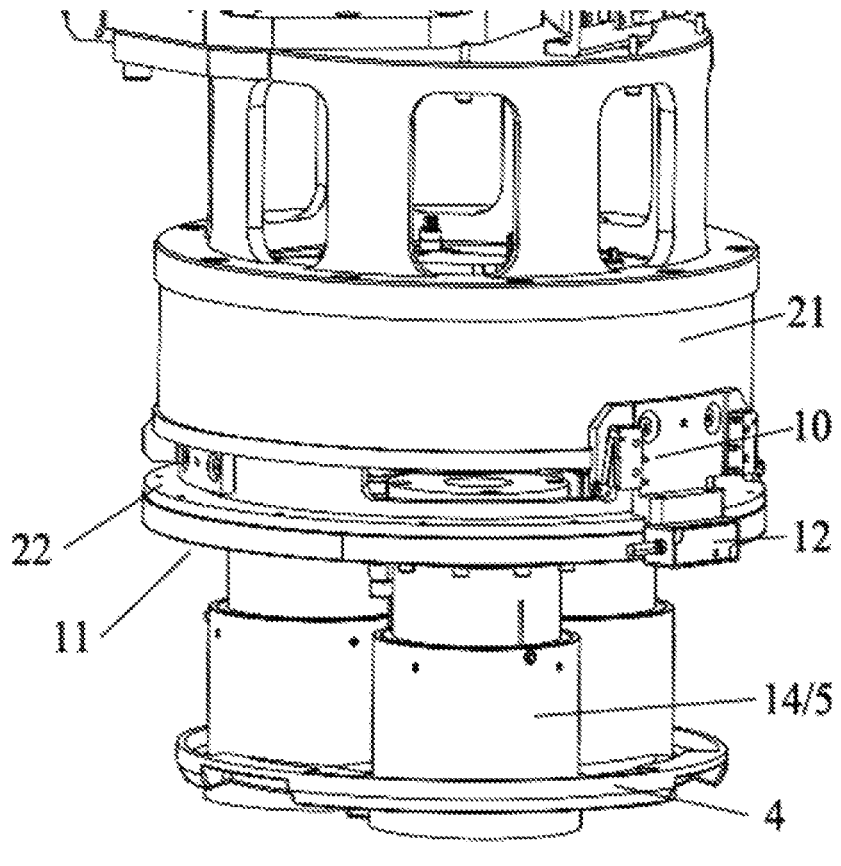
FIG. 16 is a structure view of an automatic and quick switching collimator apparatus capable of implementing accurate motion control according to an embodiment of the present disclosure.
Figure 17:
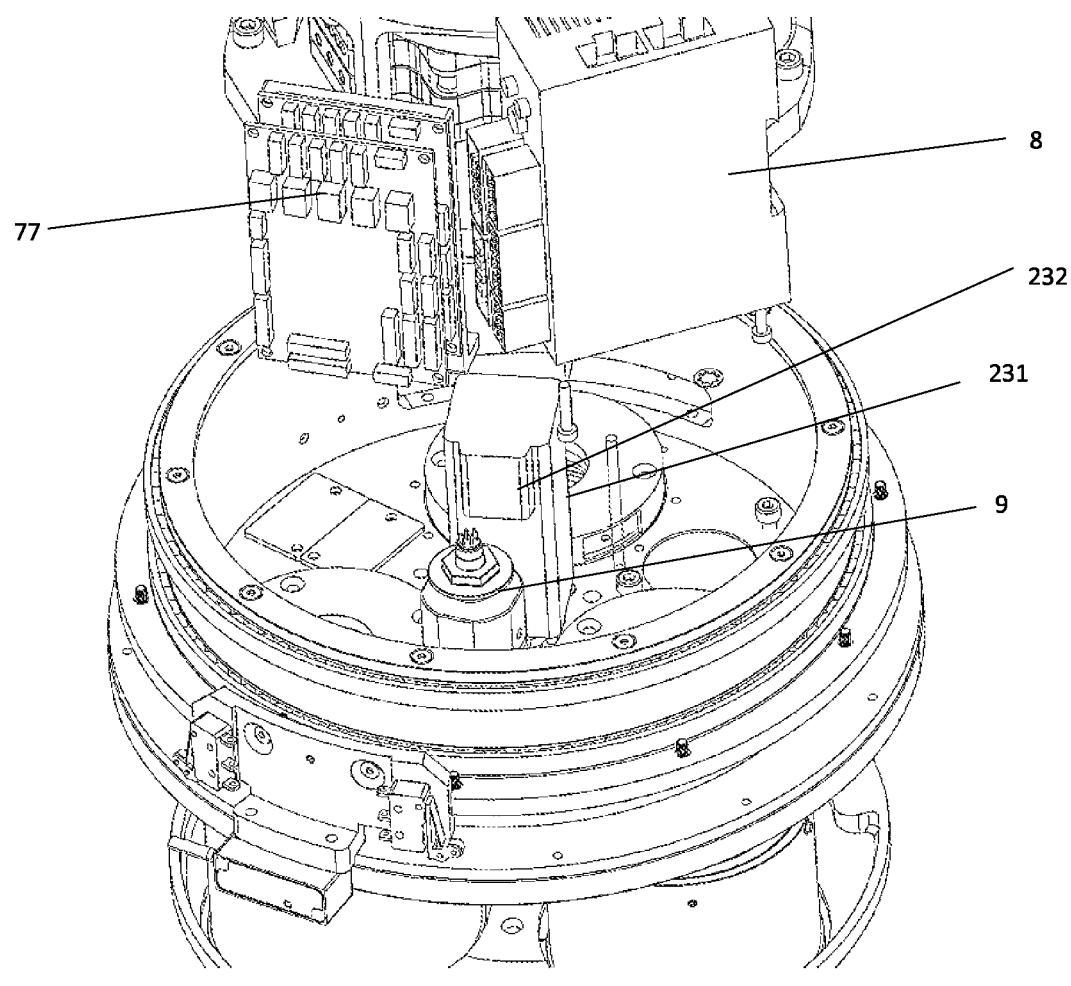
FIG. 17 is a structure view of a primary feedback positioning mechanism according to an embodiment of the present disclosure.
Figure 18:
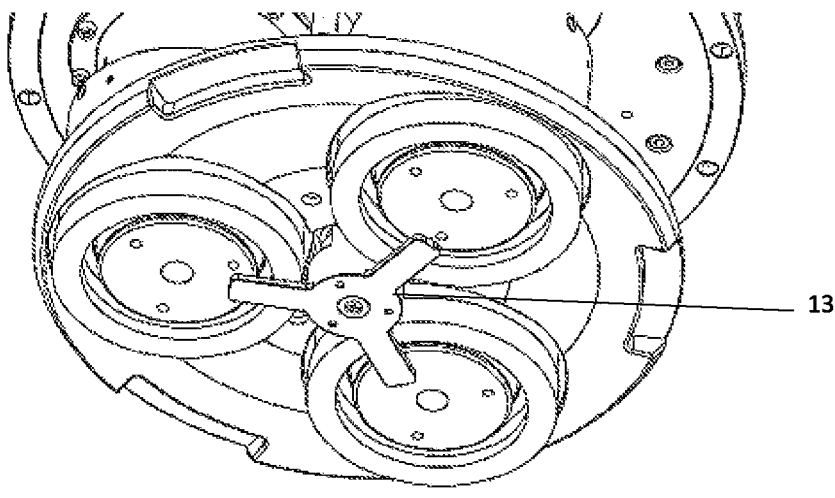
FIG. 18 is a structure view of a protection disk mechanism according to an embodiment of the present disclosure.

As shown in FIGS. 16 to 18, an automatic and quick switching collimator apparatus capable of implementing accurate motion control includes a primary position feedback mechanism, a rotation seat assembly 22, a fixing seat 21, a secondary position feedback mechanism, a collimator mechanism 14, a protection disk mechanism 4, and a control circuit 7.

The primary position feedback mechanism includes a driver 8, a stepper motor 232, a motor bracket 231, a coupling 233, and an electromagnetic push rod assembly 9. The stepper motor 232 is mounted on the motor bracket 231 and connected to the coupling 233. The coupling 233 is connected to the rotation seat assembly 22. The driver 8 and the stepper motor 232 are each an a-STEP type.

The primary position feedback mechanism has a zero-clearance type hard-block zeroing mechanism and a rotation seat bidirectional limit switch detection mechanism to implement accurate calibration of an initial zero position of the rotation seat and limit protection and alarm functions of the rotation seat. Programmable control of the driver 8 is implemented through a communication interface circuit of an isolated RS-485 to complete a station quick switching function. The station adopts a double-locking manner of motor torque lock and electromagnetic push rod lock.

The fixing seat 21 is provided with a limit switch bracket. The limit switch bracket is provided with two forward and reverse press-contact limit switches 10. The zero-clearance type hard-block zeroing mechanism of the primary position feedback mechanism refers to that the stepper motor 232 reverses zeroing at a lower speed. When a mechanical support rod structure mounted on the rotation seat collides with the limit switch bracket, the motor torque increases. When the motor torque increases to 50% of the motor load-bearing torque, this position is regarded as a motor zero point, and the zeroing process ends. The rotation seat bidirectional limit switch detection mechanism refers to that the limit switch bracket is provided with two forward and reverse press-contact limit switches 10. Except for the zeroing process, any time when the mechanical support rod structure on the rotation seat is in contact with the pressure-contact limit switches 10, the stepper motor 232 is considered to rotate beyond a circumferential rotation position. The rotation of the stepper motor 232 is stopped immediately at this time.

Through a rotor position detection sensor, the primary position feedback mechanism monitors a position of the stepper motor 232 in real time and automatically switches open-loop control and closed-loop control according to a condition. Generally, the apparatus is in an open-loop control state. The apparatus detects the action of the stepper motor 232 and meanwhile executes open-loop control. That is, the control circuit 7 calculates the number of steps in the direction in which the stepper motor 232 needs to move and sends motion information to the driver 8, and the stepper motor 232 completes the movement in the desired direction and number of steps according to an instruction of the driver 8.

When a position deviation occurs between the instruction and the position of the stepper motor 232 due to overload or the like, the closed-loop control is immediately switched to. That is, when position information fed back by a grating ruler does not match theoretical position information, the closed-loop control is turned on, thereby correcting the position and the speed. For example, a deviation between a current position and a theoretical position is calculated for the control circuit 7 to form an instruction for the motion direction and number of steps of the motor. The stepper motor 232 completes the instruction of the control circuit 7. After the stepper motor 232 completes the motion, the grating ruler feeds back a real-time position and compares the real-time position with a theoretical value. If the real-time position is in a reasonable range of the theoretical position, the stepper motor 232 stops the motion. If the real-time position is not in the reasonable range of the theoretical position, the deviation is repeatedly calculated to form a motion instruction. The stepper motor 232 completes the motion until the reading of the grating ruler is in the reasonable range of the theoretical position.

In the present disclosure, the secondary position feedback mechanism is added as a final closed-loop target on the basis of the closed-loop positioning operation of the primary position feedback mechanism to eliminate, on output positioning, the effect of deformation of transmission link (for example, coupling 233) between an output shaft of the motor and an end load.

The secondary position feedback mechanism includes a grating 11, a reading head 12, and a data collection and conversion module. The grating 11 surrounds the outer side of the rotation seat assembly 22 and is fixed by screws. When the rotor of the stepper motor 232 rotates along the axial direction of the principal axis of the stepper motor 232, the rotation seat assembly 22 drives the grating 11 to move synchronously with the rotor of the stepper motor 232. The reading head 12 and the pressure-contact limit switches 10 are mounted at the same position of the fixing seat 21, away from the beam axis direction.

The outside of the grating 11 is marked with a scale in the form of a code. The reading head 12 is mounted on the outside of the grating 11. The reading head 12 emits laser light. The grating 11 reflects the laser light with the scale code to the inside of the reading head 12. The reading head 12 receives and processes the laser light with the code scale, and then sends the laser light to the control circuit 7 through the data collection and conversion module.

A protection disk mechanism 4 is mounted at the end of a collimator 5. The protection disk mechanism 4 includes a rotatable three-leaf protection disk 13 and a proximity switch detector. A work state and a state of replacing a collimator can be switched only by rotating a nut. At the same time, the proximity switch detector is used to detect whether the protection disk mechanism 4 is in a normal protection state and output an electric signal, thereby implementing the purpose of quickly replacing the collimator.

In the protection disk mechanism 4, the rotatable three-leaf protection disk 13 is connected to other structures of the collimator apparatus through a mechanical quick connection manner and then is axially locked and fixed by six balls. The rotatable three-leaf protection disk 13 can still rotate in an angular direction, that is, in a plane perpendicular to the axial direction. When the rotatable three-leaf protection disk 13 works normally, each leaf of the rotatable three-leaf protection disk 13 rotates directly below the collimator 5 and can effectively prevent the collimator 5 from falling off to ground when locking of the collimator 5 fails. At this time, the proximity switch detector can detect that the rotatable three-leaf rotation protection disk 13 has rotated to the work position and output a "protected" signal. When the collimator 5 needs to be replaced at the end of the treatment, the leaf of the rotatable three-leaf protection disk 13 rotates to the middle of two collimators 5. This part no longer blocks disengagement and entry of the collimator 5 and does not affect the replacement of the collimator 5. At this time, the proximity switch does not detect that the rotatable three-leaf protection disk 13 is in the work position and outputs an "unprotected" signal. When a collimator 5 has been replaced, the rotatable three-leaf protection disk 13 is rotated to a position (work position) directly below the collimator 5. This mechanism recovers the protection function of the collimator 5. The proximity switch detects a signal that the rotatable three-leaf protection disk 13 is in the work position and outputs a "protected" signal.

The collimator mechanism 14 includes at least two collimators 5 and a probe PCB board. The collimator mechanism 14 is connected to the rotation seat assembly 22. A groove is disposed above the collimator 5. A metal probe is disposed on the probe PCB board. The outer diameter of the PCB board is less than the outer diameter of the collimator barrel. The inner diameter of the PCB board is greater than the inner diameter of the collimator barrel with the maximum aperture. The collimator 5 has a symmetrical locking structure. Thus, the positioning error caused by an asymmetrical locking structure can be effectively avoided. For a specific locking manner, reference is made to the previous embodiment.

The control circuit 7 includes a power module, a communication module connected to an upper-stage system, a collimator physical code module, an electromagnetic push rod driving and position feedback module, and a protection disk detection module. The control circuit 7 is externally connected to the reading head 12 and an a-STEP driver. The a-STEP driver is directly connected to an a-STEP stepper motor to control movement of the rotation seat assembly 22 with multiple stations.

The total input terminal of the power module is designed with a transient voltage suppressor (TVS) diode circuit configured to protect the control circuit 7 from electrostatic discharge, effectively suppressing the surge impact of 400 W (10/1000 μs). The power module adopts a two-stage isolation mechanism. One stage of isolation mechanism is isolation of power supply from control supply. The control supply is implemented by converting the power supply through a step-down isolation DC/DC (direct current to direct current) power supply. Another stage of isolation mechanism is isolation of communication power supply from the control supply. The communication power supply is implemented by converting the control supply through an isolated communication chip.

Figure 19:
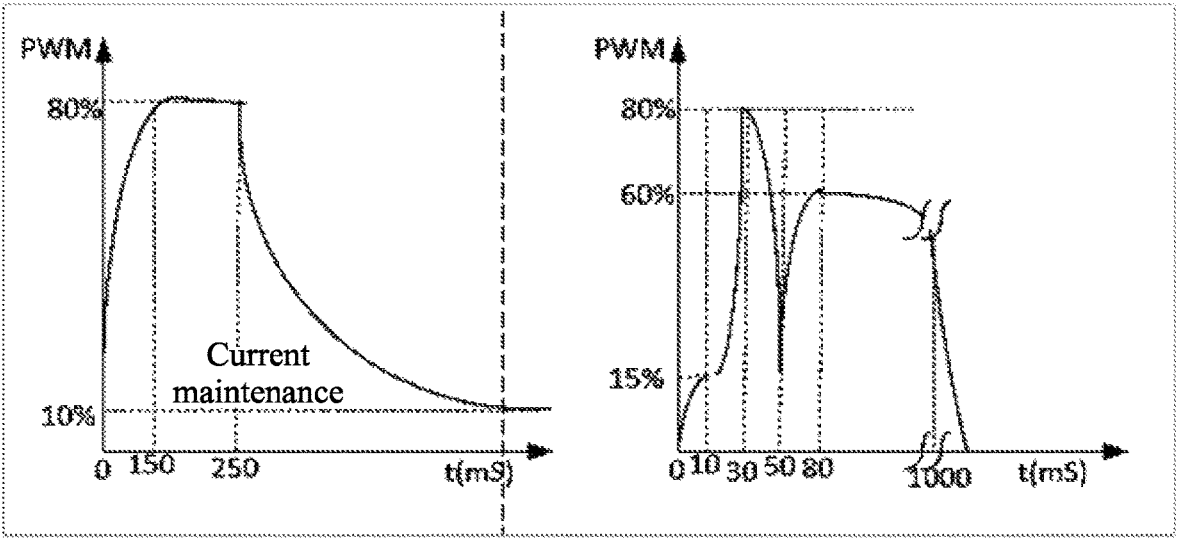
FIG. 19 is a graph of current versus time when the electromagnetic pin is turned on and turned off according to an embodiment of the present disclosure.

As shown in FIG. 19, the electromagnetic push rod driving and position feedback module is designed with PWM technology. The pulse width is adjusted in the range of 0 to 300 microseconds. To minimize mechanical impact and reduce a coil current after an electromagnetic push rod is sucked to ensure that power consumption does not exceed the limit, the coil current needs to be reduced to 10% of a rated value in time after the electromagnetic push rod is sucked in place at the moment of current opening, so as to ensure that the coil works continuously at 24 V voltage. Through adjusting PWM duty cycle in real time in the suction process, continuous adjustment of instantaneous high-power suction and continuous low-power current maintenance after suction in place can be implemented. The PWM duty cycle also needs to be adjusted in real time during current shutdown to achieve slow release effect and reduce mechanical impact.

Figure 20:
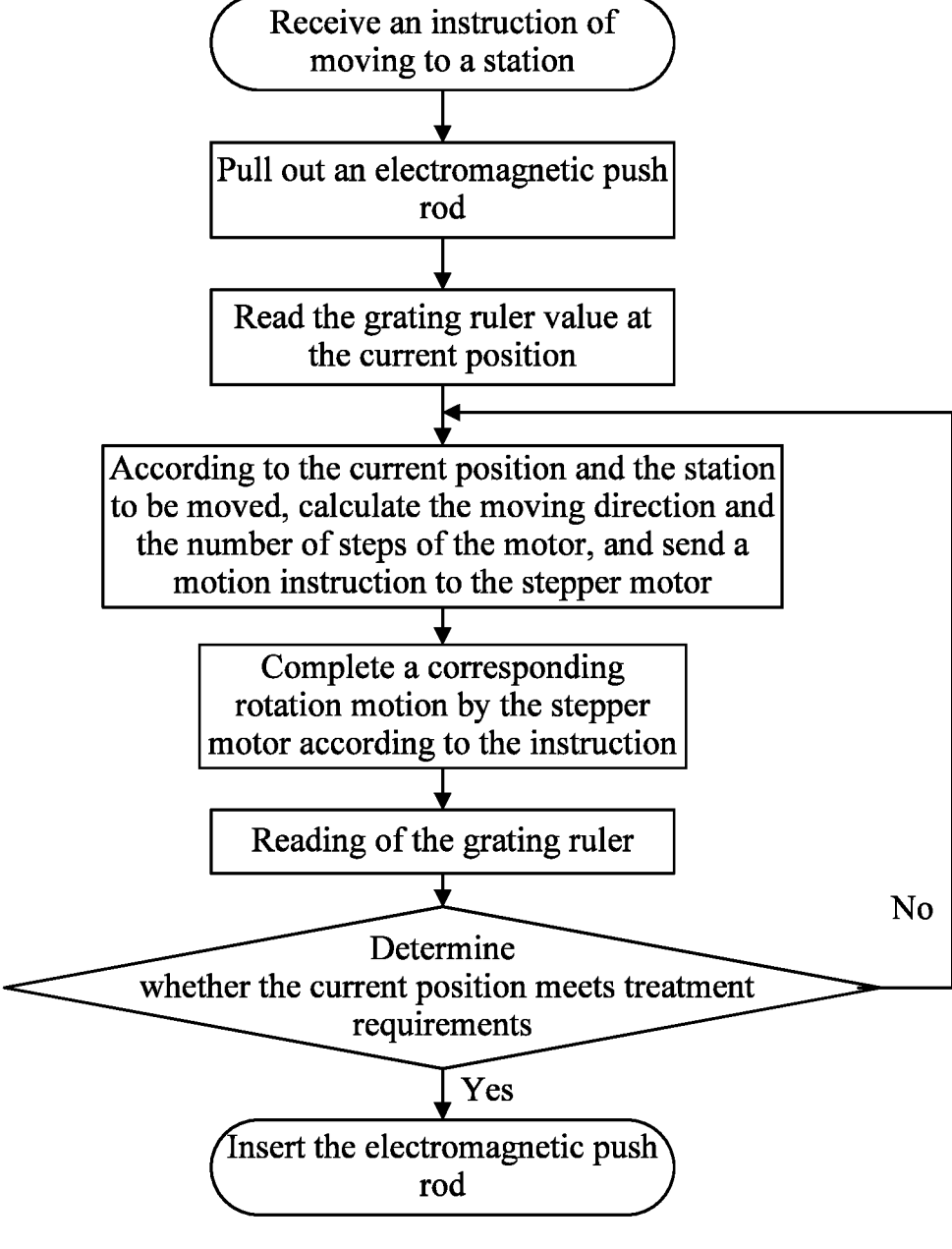
FIG. 20 is a flowchart of an accurate motion control method according to an embodiment of the present disclosure.

An embodiment of the present disclosure provides a motion control method. As shown in FIG. 20, motor zero point initialization is completed through hard-block and limit switch detection mechanism. Motor initialization processing is performed according to the grating reading fed back by a secondary position feedback mechanism and the theoretical value obtained by a primary position feedback mechanism. The primary position feedback mechanism implements primary automatic motion, automatic positioning and locking by relying on an a-STEP closed loop. The secondary position feedback mechanism feeds back position information in real time. The primary position feedback mechanism performs compensation motion and deviation correction according to the position information to implement a two-stage closed-loop control. The steps are as follows.

(1) Motor zero point initialization is performed.

(2) A grating position value of a preset position is used as a theoretical value of the preset position obtained by the primary position feedback mechanism. In the case where a stepper motor stops moving according to the theoretical value of the preset position, and a grating reading of a stop position of the stepper motor fed back by the secondary position feedback mechanism is consistent with the theoretical value of the preset position, the theoretical value of the preset position is used as an initial theoretical value of the motor, and the motor initialization ends.

(3) An upper computer sends a command to a control circuit, the control circuit feeds back the command to an a-STEP driver, and the driver sends a motion instruction to the stepper motor according to the command. A push rod lock detection switch is closed. An electromagnetic push rod of the primary position feedback mechanism is powered on. A coil current is reduced to 10% of a rated value in real time. The electromagnetic push rod is pulled out of the fixing seat.

(4) An a-STEP stepper motor implements angular ultra-high resolution and sufficient motor output torque at an ultra-high deceleration ratio of 100:1 to implement primary motion positioning. Data of a subdivided rotation encoder built into the a-STEP stepper motor is fed back to a driving front stage through a decelerator and a transmission mechanism to implement a first-stage closed-loop control. A first-stage closed-loop network is inserted into a biquad filtering algorithm to effectively eliminate subdivision clearance and transmission jitter and ensure smooth positioning of the a-STEP stepper motor.

(5) After the movement is in place, the push rod lock detection switch is turned off. The control circuit adjusts a PWM duty cycle. The electromagnetic push rod moves smoothly to the fixing seat to implement primary accurate positioning and locking. The control circuit returns motion information to the a-STEP driver.

(6) A reading head reads a grating position in real time. A read grating reading and the range of a theoretical position Δ are determined.

(7) In the case where a difference between the grating reading and a target constant deviates from the range of the theoretical position Δ, the control circuit sends a correction command to the stepper motor and the driver to move a collimator to a station position where the collimator needs to move and correct angle deviation to implement a second-stage closed-loop control. In this embodiment, the range of the theoretical position Δ is ±0.018°.

(8) After the rotation seat assembly stops moving, the difference between the grating reading and the target constant is in the range of the theoretical position Δ. The electromagnetic push rod is locked in a hole. A micro switch is triggered to return an in-place signal to the upper computer.

The rotation seat assembly has two forward and reverse rotation over-range limit points. The motor zero point initialization includes detecting a relative position of the rotation seat assembly and the fixing seat by using a micro switch, setting a reverse rotation over-range limit point of the rotation seat assembly as a positioning origin, and searching for the positioning origin by using a press-contact mode supported by the driver; and observing along a direction from the end face of the rotation seat assembly facing away the beam hole to the beam hole, i.e., against the beam hole direction, when the rotation seat assembly rotates clockwise (forward), the grating reading and a motor encoder reading increases, and when the rotation seat assembly rotates counterclockwise (reversely), the grating reading and the motor encoder reading decreases. The rotation seat assembly rotates reversely to find the positioning origin. After the positioning origin is determined, the rotation seat assembly rotates forward. 1# station, 2# station, blind hole, and 3# station pass through the beam hole in turn.

Figure 21:
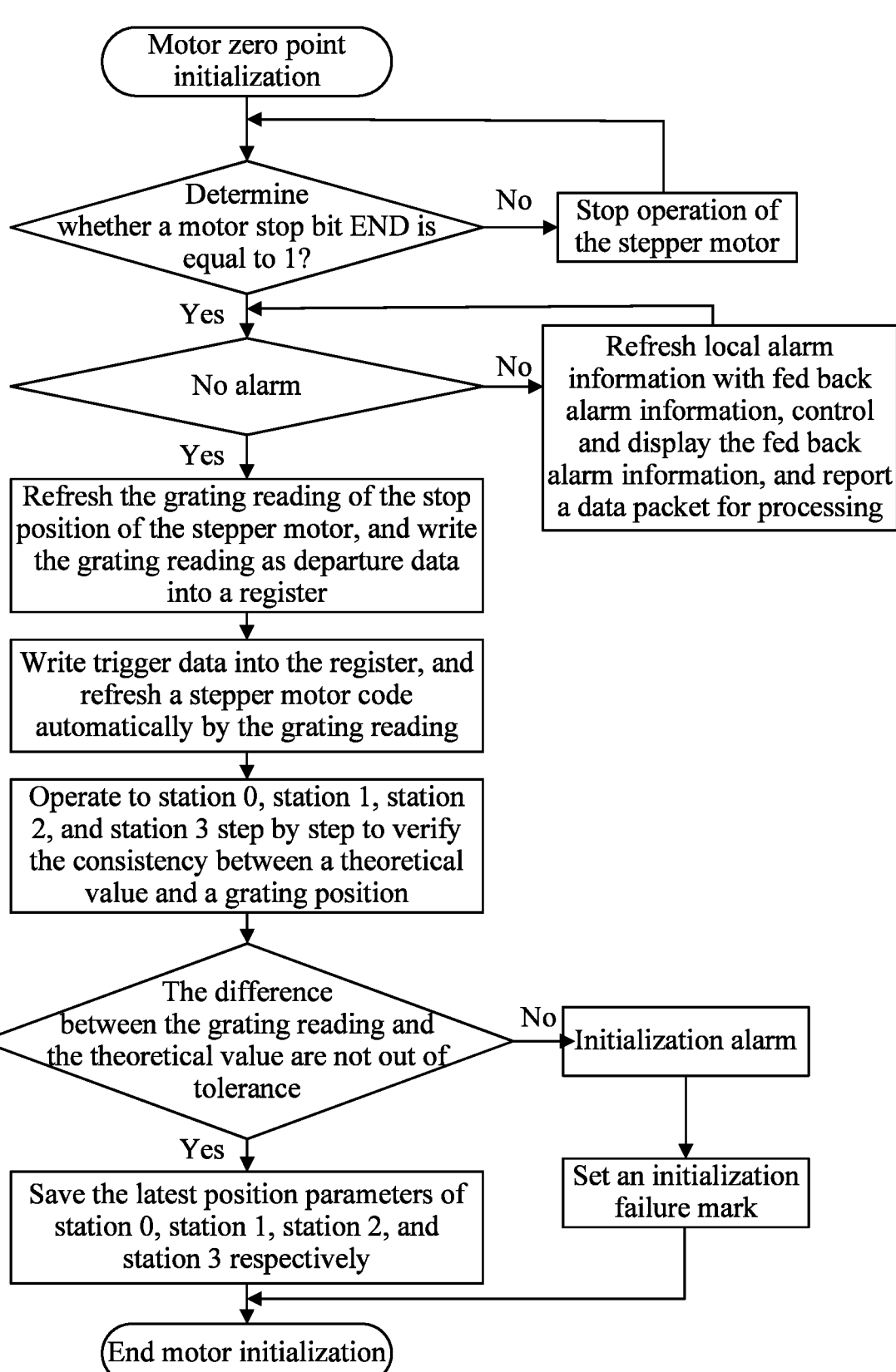
FIG. 21 is a flowchart of a motor initialization processing method according to an embodiment of the present disclosure.

As shown in FIG. 21, a motor initialization flow is as follows.

(1) After motor zero point initialization is performed, the control circuit obtains a motor stop bit END. It is determined that whether the motor stop bit END is equal to 1. No alarm is given in response to the motor stop bit END being equal to 1. In response to the motor stop bit END being not equal to 1, operation of the stepper motor is stopped, and alarm information is fed back.

(2) In the case of no alarm, the control circuit refreshes the grating reading of the stop position of the stepper motor and writes the grating reading as departure data into a register. The stepper motor automatically updates the grating position value of a preset position according to the departure data. The grating position value of the preset position is used as the theoretical value of the preset position. In the case of giving an alarm, the control circuit refreshes local alarm information with fed back alarm information, controls and displays the fed back alarm information, and reports a data packet for processing. The preset position includes multiple stations.

(3) After the stepper motor executes a motion command to operate to each station, conformity between the grating reading of the stop position of the stepper motor and a theoretical value of the each station is verified. The conformity includes a comparison of a difference between the grating reading and the theoretical value with a preset difference range. The motion command includes a theoretical value of each station.

(4) If the difference between the grating reading and the theoretical value is in the range of the preset difference, the grating reading is saved as a position parameter of the each station, and the motor initialization ends. If the difference between the grating reading and the theoretical value is not in the range of the preset difference, initialization error reporting is executed, an initialization failure mark is set, and the motor initialization ends.

The present disclosure has the effects below.

1. According to the present disclosure, multiple secondary collimators with different apertures mounted on a rotation seat assembly in an accelerator head are provided. At least two collimators are mounted on a treatment head at the same time. During a treatment process, the treatment head can quickly switch collimators according to a treatment plan, overcoming the disadvantage of time delay in replacing the collimators in the related art. In most cases, a collimator can be replaced without stopping the treatment. 2. According to the present disclosure, through automatic rotation, automatic identification, and automatic locking of the rotation seat assembly, quick switching of different collimators is implemented, and treatment time is saved. 3. According to the present disclosure, the blind-hole collimator is mounted on the rotation seat assembly. The position of the blind-hole collimator is rotated selectively in the state of non-ray irradiation in the treatment fraction to greatly block a dark current and reduce the damage of the dark current to a patient. 4. According to the present disclosure, the transmission system adopts a direct transmission manner, in which a stepper motor is used to directly drive a shaft to rotate. The number of transmission stages is reduced, and the transmission accuracy and efficiency can be improved. The structure is compact and meets space limitation requirements. Automatic positioning, identification, and lock are implemented. At the same time, the stepper motor converts an electric pulse into an angular displacement and can control the angular displacement by controlling the number of pulses to achieve the purpose of accurate positioning. There is no accumulated error, and the repeated positioning accuracy is high. Thus, positioning accuracy requirements can be met. 5. According to the present disclosure, the collimator is fixed in a ball locking manner. There is three-stage locking protection. Automatic locking is performed through the ball. The protective function can be achieved during both normal and failure of the spring. It can be ensured that a secondary collimator is mounted and locked in place, thereby ensuring safety and reliability. 6. According to the present disclosure, the accurate motion control method and the collimator identification method provided significantly improve the automation degree, accuracy, reliability, and safety of an entire apparatus. 7. According to the present disclosure, the accurate calibration of an initial zero position of the rotation seat is implemented through a bidirectional limit switch. A primary position feedback mechanism and a secondary position feedback mechanism are adopted to implement a two-stage closed-loop control of the rotation seat assembly. The direct measurement value of the grating is accurate, thereby eliminating the error caused by part deformation caused by overload of the collimator in the transmission link. 8. The collimator is protected by using a rotatable three-leaf protection disk. Through reasonable structure control, the operation is convenient, and the collimator can be replaced without removal. Thus, the replacement time is reduced, and the treatment time is saved.

What is claimed is:

1. A collimator apparatus, comprising a transmission assembly and at least two collimators, wherein the transmission assembly is connected to the at least two collimators, and the transmission assembly is configured to implement automatic switching of different collimators through rotation action; and wherein the collimator apparatus further comprises at least two assembly components, wherein each of the at least two assembly components is provided with a respective one of the at least two collimators, the transmission assembly is connected to the each of the at least two assembly components, the transmission assembly is configured to drive different assembly components through rotation to implement automatic switching of different collimators, and the transmission assembly comprises a rotation seat assembly, a fixing seat, a motor assembly, and an electromagnetic pin assembly, wherein the motor assembly and the fixing seat are connected to the rotation seat assembly, the fixing seat is provided with a beam hole, and the rotation seat assembly is configured to, under driving of the motor assembly, drive the at least two assembly components to move to rotate a designated one of the at least two collimators to a position facing the beam hole; and the electromagnetic pin assembly is configured to automatically position, identify, and lock the rotation seat assembly, the electromagnetic pin assembly comprises an electromagnetic pin, a mounting ring, and first micro switches; the electromagnetic pin is fixed to the rotation seat assembly by the mounting ring and rotates with the rotation seat assembly, the electromagnetic pin is energized in a case where the motor assembly drives the rotation seat assembly to rotate, and a metal rod of the electromagnetic pin retracts into the electromagnetic pin; the electromagnetic pin is de-energized in a case where the motor assembly has driven the rotation seat assembly to rotate to a desired position, and the metal rod extends out of the electromagnetic pin and is inserted into a tapered hole of the fixing seat so that the rotation seat assembly is not allowed to rotate; and the metal rod is in contact with one of the first micro switches at a corresponding position, the one of the first micro switches is triggered, and in the case where the one of the first micro switches is triggered, the one of the first micro switches is configured to send an electrical signal to allow a system to identify a type of one of the at least two collimators facing a center of the beam hole.

2. The collimator apparatus according to claim 1, wherein the rotation seat assembly comprises a rotation seat, a bearing inner race end cap, two thin-wall bearings, and a bearing outer race end cap;

the two thin-wall bearings are mounted between the rotation seat and the fixing seat, outer walls of the two thin-wall bearings are provided with the bearing outer race end cap and the bearing inner race end cap, and the rotation seat is configured to rotate through the two thin-wall bearings under action of the motor assembly; and the outer walls of the two thin-wall bearings, the bearing outer race end cap, and the bearing inner race end cap are configured to fix the two thin-wall bearings; in a case where the at least two collimators are disposed at a lower end of the collimator apparatus, the bearing outer race end cap is configured to bear a gravity of the collimator; and in a case where the at least two collimators are disposed at an upper end of the collimator apparatus, the bearing inner race end cap is configured to bear the gravity of the collimator, wherein the at least two collimators are each a secondary collimator.

3. The collimator apparatus according to claim 2, wherein at least one blind-hole collimator and at least two circular holes are disposed on the rotation seat assembly, the at least one blind-hole collimator is mounted on the rotation seat, and the at least two circular holes are equally distributed and configured to fixedly connect the at least two assembly components; the at least one blind-hole collimator is disposed in the middle of two of the at least two circular holes and on a same circumference as the at least two assembly components, and the motor assembly is further configured to, in a non-therapeutic state, drive the rotation seat assembly to rotate to control one of the at least one blind-hole collimator to switch to the position facing the beam hole.

4. The collimator apparatus according to claim 2, wherein the electromagnetic pin is a push-pull electromagnetic pin in a normally closed state; in a case where the electromagnetic pin is de-energized, the metal rod keeps a state of extending out of the electromagnetic pin; in a case where the electromagnetic pin is energized, the metal rod retracts into the electromagnetic pin; and a number of the first micro switches is equal to a sum of a number of blind-hole collimators and a number of circular holes, the first micro switches are fixed to the fixing seat, and each of the blind-hole collimators corresponds to a respective one of the first micro switches, and each of the circular holes corresponds to a respective one of the first micro switches.

5. The collimator apparatus according to claim 1, wherein the each of the at least two assembly components further comprises a collimator identification assembly and a locking assembly; and the locking assembly comprises a spring, an outer sleeve, an inner tapered sleeve, and a ball, the outer sleeve is fixed with the inner tapered sleeve, the inner tapered sleeve is in contact with the ball, the ball is in contact with a ball groove of the respective one of the at least two collimators, and the spring is disposed below the inner tapered sleeve and is connected to the inner tapered sleeve;

the inner tapered sleeve is provided with three tapered surface portions which are a first tapered surface, a second tapered surface, and a third tapered surface, wherein in a portion where the first tapered surface is disposed, a cross-sectional area of the inner tapered sleeve gradually decreases from up to down; in a portion where the second tapered surface is disposed, a cross-sectional area of the inner tapered sleeve gradually increases from up to down; and in a portion where the third tapered surface is disposed, a cross-sectional area of the inner tapered sleeve gradually decreases from up to down; and the first tapered surface is tangential to the ball when the first tapered surface is in contact with the ball, the second tapered surface is tangential to the ball when the second tapered surface is in contact with the ball, and the ball is tangential to two tapered angles of the ball groove of the respective one of the at least two collimators.

6. The collimator apparatus according to claim 5, wherein the locking assembly has a three-stage locking manner comprising two-stage mechanical locking and one-stage locking check protection;

a first-stage mechanical locking manner is that in a case where the spring is in a normal work state, the spring is configured to apply a pressure to the inner tapered sleeve to make the ball effectively contact with the first inner tapered surface of the inner tapered sleeve and make the first tapered surface press the ball to lock the respective one of the at least two collimators; and a second-stage mechanical locking manner is that in a case where the spring loses a pulling force to the inner tapered sleeve, the outer sleeve and the inner tapered sleeve move upward, the ball no longer presses the respective one of the at least two collimators, the respective one of the at least two collimators moves downward for a certain distance until the second tapered surface of the inner tapered sleeve re-presses an outermost ball, and the ball re-presses the ball groove of the respective one of the at least two collimators to implement second-stage mechanical locking of the respective one of the at least two collimators so that the respective one of the at least two collimators does not fall off;

the collimator apparatus further comprises a position sensor, and the position sensor is disposed at a distance from a metal sheet on the outer sleeve; and the one-stage locking check protection manner is that in a case where the respective one of the at least two collimators is locked and the outer sleeve is pulled along a preset direction, the metal sheet on the outer sleeve approaches the position sensor, and the position sensor is configured to detect the sheet metal so that the collimator is mounted and locked in place, wherein the respective one of the at least two collimators is a secondary collimator, and the preset direction is a direction in which the respective one of the at least two collimators is disengaged from the each of the at least two assembly components; and a collimator mounting and locking manner is that the respective one of the at least two collimators is mounted in the each of the at least two assembly components, the outer sleeve is pulled downward by hand to make the inner tapered sleeve press the ball so that the ball presses a groove of the respective one of the at least two collimators to lock the respective one of the at least two collimators; and in a case of replacing the respective one of the at least two collimators, the respective one of the at least two collimators is held by hand, and the outer sleeve is pushed upwards to make the ball move to release a locking state so that the respective one of the at least two collimators is disengaged from the each of the at least two assembly components.

7. The collimator apparatus according to claim 5, wherein the collimator identification assembly comprises a concave portion and a convex portion which are disposed on a top surface of a collimator, a probe with a telescoping spring, and a code identification circuit; and the collimator identification adopts a physical code manner, the concave portion or the convex portion is disposed at a corresponding position on the top surface of the collimator, and the probe with the telescoping spring is disposed above the collimator, corresponds to the concave portion and the convex portion, and is configured to detect a corresponding electrical signal; in a case where the concave portion is located below the probe, the probe is not in contact with the collimator, no current passes through the probe, and a voltage signal is 1; and in a case where the convex portion is located below the probe, the probe is in contact with the collimator, a current passes through the probe, and a voltage signal is 0, wherein the collimator is a secondary collimator.

8. The collimator apparatus according to claim 7, wherein at different radii of the top surface of the collimator, a number of concave portions and convex portions are machined, the number of concave portions and convex portions are configured to be identified to form a binary code, and different types of collimators use different codes; the probe is disposed on a printed circuit board (PCB), and the code identification circuit is configured to identify a type of the collimator through a code composed of voltage signals.

9. The collimator apparatus according to claim 1, wherein each of the at least two collimators is provided with a concave portion, a convex portion, and a ball groove; an angle of the ball groove is tangential to a ball configured for locking.

10. A collimator apparatus, comprising a transmission assembly and at least two collimators, wherein the transmission assembly is connected to the at least two collimators, and the transmission assembly is configured to implement automatic switching of different collimators through rotation action; and wherein the transmission assembly comprises a rotation seat assembly, a primary position feedback mechanism, and a fixing seat, and the collimator apparatus further comprises a secondary position feedback mechanism and a control circuit;

the at least two collimators are each a secondary collimator, and mounted on the rotation seat assembly, and the rotation seat assembly is configured to drive the at least two collimators to rotate to allow a designated one of the at least two collimators to rotate to a position facing a beam hole;

the primary position feedback mechanism comprises a rotor position detection sensor, a driver, and a stepper motor, the stepper motor is connected to the rotation seat assembly and configured to drive the rotation seat assembly to rotate under an instruction of the driver, and the rotor position detection sensor is configured to monitor a position of the stepper motor in real time and automatically switch open-loop control and closed-loop control according to a condition; and the secondary position feedback mechanism comprises a grating, a reading head, and a data collection and conversion module; and the reading head is configured to read a scale code of the grating and transmit the scale code to the control circuit through the data collection and conversion module.

11. The collimator apparatus according to claim 10, wherein the primary position feedback mechanism further comprises a motor bracket, a coupling, and an electromagnetic push rod component; and the stepper motor is mounted on the motor bracket and connected to the coupling, and the coupling is connected to the rotation seat assembly, wherein the primary position feedback mechanism has a zero-clearance type hard-block zeroing mechanism and a rotation seat bidirectional limit switch detection mechanism, the primary position feedback mechanism is configured to implement calibration of an initial zero position of the rotation seat through a hard block disposed on the fixing seat, and the primary position feedback mechanism is further configured to implement limit protection and alarm functions of the rotation seat through two forward and reverse rotation over-range limit switches disposed on the fixing seat; and the primary position feedback mechanism is further configured to implement programmable control of the driver through a communication interface circuit of an isolated recommended standard RS-485 to complete switching of a station, wherein the station adopts a double-locking manner of motor torque locking and electromagnetic push rod locking.

12. The collimator apparatus according to claim 11, wherein a control manner of the primary position feedback mechanism comprises an open-loop control and a closed-loop control, use time of the open-loop control is longer than use time of the closed-loop control, and the primary position feedback mechanism is further configured to execute the open-loop control in a case where an action of the stepper motor is detected in real time; and the primary position feedback mechanism is further configured to, in a case of an instruction and a position offset of the stepper motor due to overload, switch the open-loop control to the closed-loop control to correct position and speed; and the secondary position feedback mechanism is configured to add, on a basis of closed-loop positioning operation of the primary position feedback mechanism, the secondary position feedback mechanism as a final closed-loop target to eliminate, on output positioning, the effect of deformation of transmission link between an output shaft of the stepper motor and an end load.

13. The collimator apparatus according to claim 10, further comprising a protection disk mechanism, wherein the protection disk mechanism comprises a rotatable multi-leaf protection disk and a proximity switch detector, and the rotatable multi-leaf protection disk is connected to the collimator apparatus through a mechanical quick connection manner and rotatable in an angular direction; in a case where the rotatable multi-leaf protection disk works normally, each leaf of the rotatable multi-leaf protection disk rotates directly below a respective one of the at least two collimators and is configured to prevent the respective one of the at least two collimators from falling off to ground when locking fails; the proximity switch detector is configured to detect that the rotatable multi-leaf protection disk rotates to a work position and to output a corresponding signal; in a case where a collimator needs to be replaced after treatment, each leaf of the rotatable multi-leaf protection disk is rotated to the middle of respective two of the at least two collimators and is configured to no longer block disengagement and entry of the collimator, and the proximity switch detector is further configured to output a corresponding signal in a case where the rotatable multi-leaf protection disk is not detected in the work position; and in a case where the collimator has been replaced, the rotatable multi-leaf protection disk is rotated directly below a collimator to restore a protection function of the collimator, and the proximity switch detector is further configured to detect a signal of the rotatable multi-leaf protection disk being in the work position and output a corresponding signal.

14. The collimator apparatus according to claim 10, wherein the driver is an a-STEP driver, the stepper motor is an a-STEP stepper motor, the control circuit is connected to the reading head and the a-STEP driver, and the a-STEP driver is directly connected to the a-STEP stepper motor to control motion of the rotation seat assembly with multiple stations;

the control circuit comprises a power module, a communication module, a collimator physical code module, an electromagnetic push rod driving and position feedback module, and a protection disk detection module;

the power module adopts a two-stage isolation mechanism, wherein one stage of isolation mechanism is to isolate power supply from control supply, and the control supply is implemented by DC/DC conversion of the power supply through a step-down isolation DC/DC power supply; and another stage of isolation mechanism is to isolate communication power supply from the control supply, and the communication power supply is implemented by converting the control supply through an isolated communication chip; and the electromagnetic push rod driving and position feedback module is designed by using pulse width modulation (PWM), with a pulse width adjustment range of 0 to 300 μs; the electromagnetic push rod driving and position feedback module is configured to reduce a coil current to 10% of a rated value in time after the electromagnetic push rod is sucked in place at the moment of current opening to allow a coil to work continuously; through adjusting a PWM duty cycle in real time in a suction process, continuous adjustment of instantaneous high-power suction and continuous low-power current maintenance after in-place suction are implemented; and the PWM duty cycle is adjusted in real time during current shutdown to reduce mechanical impact.

15. A motion control method, applied by the collimator apparatus according to claim 1, wherein a stepper motor in the motor assembly directly drives a coupling in the motor assembly to rotate, the coupling is connected to the rotation seat assembly, the coupling absorbs eccentricity caused during movement, and the method comprises:

reading a planning sequence output by an upper computer software, and reading a preset collimator sequence;

in a case where a plurality of preset collimators are loaded into the at least two assembly components in a one-to-one manner, determining whether a collimator at a position of a beam axis corresponds to the preset collimator sequence; in response to the collimator at the position of the beam axis corresponding to the preset collimator sequence, executing the planning sequence, and in response to the collimator at the position of the beam axis not corresponding to the preset collimator sequence, turning a collimator corresponding to a first preset position, a second preset position, or a third preset position to the position of the beam axis; and in a case where a collimator at a preset position is successfully turned to the position of the beam axis, sending an in-place signal, and in a case where the collimator at the preset position fails to be turned to the position of the beam axis, reporting a fault signal, wherein the beam axis is an axis of the beam hole;

determining whether execution of the planning sequence output by the upper computer software is completed, and in response to the execution of the planning sequence being completed, ending a current control; and in response to the execution of the planning sequence not being completed, returning to execute the operations of reading the planning sequence output by the upper computer software, reading the preset collimator sequence, and determining whether a current collimator at the position of the beam axis corresponds to the preset collimator sequence.

16. The motion control method according to claim 15, wherein a rotation seat of the rotation seat assembly is provided with a limit block, and after the stepper motor receives a command to drive the rotation seat to rotate, the limit block rotates along with the rotation seat to determine an initial position, wherein a positioning flow of the stepper motor comprises:

determining whether the stepper motor is in a ready state; in response to the stepper motor being in the ready state, performing a next operation; and in response to the stepper motor being not in the ready state, reporting a fault, and ending a current positioning flow;

determining whether a current position is consistent with a preset position; in response to the current position being consistent with the preset position, ending a current positioning flow; and in response to the current position being inconsistent with the preset position, executing a next operation;

rotating a position of the collimator to determine whether the collimator has been rotated to the preset position; in response to the collimator having been rotated to the preset position, a ready state of reaching the preset position according to a preset process is entered; and in response to the collimator not rotating to the preset position, controlling the stepper motor to rotate to allow the collimator to reach the preset position;

in a case where the collimator times out and does not reach the preset position, reporting a fault;

the electromagnetic pin being matched with the stepper motor to implement positioning, identification, and locking, and the electromagnetic pin being fixed to the rotation seat by the mounting ring and rotating with the rotation seat, wherein the electromagnetic pin comprises N first micro switches, N is a natural number greater than or equal to three, and N is equal to a sum of a number of blind hole-collimators and a number of collimators, wherein N−1 first micro switches of the N first micro switches are fixed on the fixing seat, positions of the N−1 first micro switches correspond to N−1 collimators in a one-to-one manner, and the other one of the N first micro switches corresponds to the blind-hole collimator; the electromagnetic pin being a push-pull electromagnetic pin in a normally closed state; in a case where the electromagnetic pin is de-energized, the metal rod keeping a state of extending out of the electromagnetic pin; and in a case where the electromagnetic pin is energized, the metal rod retracting into the electromagnetic pin.

17. The motion control method according to claim 15, wherein a flow for implementing automatic positioning, identification, and locking of the electromagnetic pin comprises:

in a case where the motor assembly drives the rotation seat assembly to rotate, energizing the electromagnetic pin so that the metal rod retracts into the electromagnetic pin;

in a case where the rotation seat assembly is rotated to a desired position, de-energizing the electromagnetic pin so that the metal rod extends out of the electromagnetic pin and is inserted into the tapered hole of the fixing seat, thereby blocking rotation of the rotation seat assembly; and when the metal rod of the electromagnetic pin is in contact with one of the N first micro switches at a corresponding position, triggering the one of the N first micro switches to detect whether the electromagnetic pin is locked in place to determine a station below the beam axis.

18. A motion control method, applied to the collimator apparatus according to claim 10, comprising:

completing motor zero point initialization through a hard block and a limit switch detection mechanism, and performing motor initialization processing according to a grating reading fed back by the secondary position feedback mechanism and a theoretical value obtained by the primary position feedback mechanism; and implementing primary automatic motion, automatic positioning, and locking by the primary position feedback mechanism by means of an a-STEP closed loop, feeding back position information by the secondary position feedback mechanism in real time, and performing compensation motion and deviation correction by the primary position feedback mechanism according to the fed back position information to implement a two-stage closed-loop control.

19. The motion control method according to claim 18, wherein performing motor initialization processing according to the grating reading fed back by the secondary position feedback mechanism and the theoretical value obtained by the primary position feedback mechanism comprises:

using a grating position value of a preset position as a theoretical value of the preset position obtained by the primary position feedback mechanism, in a case where the stepper motor stops moving according to the theoretical value of the preset position, and a grating reading of a stop position of the stepper motor fed back by the secondary position feedback mechanism is consistent with the theoretical value of the preset position, using the theoretical value of the preset position as an initial theoretical value of the motor, and ending the motor initialization; and implementing primary automatic motion, automatic positioning, and locking by the primary position feedback mechanism by means of the a-STEP closed loop, feeding back the position information by the secondary position feedback mechanism in real time, and performing compensation motion and deviation correction by the primary position feedback mechanism according to the fed back position information to implement the two-stage closed-loop control comprises:

receiving, by the control circuit, a command sent by an upper computer and feeding back the command to the driver, sending, by the driver, a motion instruction to the stepper motor according to the command, making a push rod lock detection switch closed, powering on an electromagnetic push rod of the primary position feedback mechanism, reducing a coil current to 10% of a rated value, and pulling the electromagnetic push rod out of the fixing seat, wherein the driver is an a-STEP driver;

implementing angular resolution and motor output torque by the stepper motor at a deceleration ratio of 100:1 to implement primary motion positioning; and feeding back data of a subdivided rotation encoder built into the stepper motor to a driving front stage through a decelerator and a transmission mechanism to implement a first-stage closed-loop control, wherein the stepper motor is an a-STEP stepper motor;

after the collimator moves in place, turning off the push rod lock detection switch, adjusting a pulse width modulation (PWM) duty cycle by the control circuit, the electromagnetic push rod moving to the fixing seat to implement primary positioning and locking, and returning motion information by the control circuit to the driver;

reading a grating position by the reading head in real time, and determining a read grating reading and a range of a theoretical position $\Delta$;

calculating, by the control circuit, a motion direction of the motor and a number of steps of the motor according to a current position of the collimator and a station position where the collimator needs to move, and sending a motion instruction to the stepper motor; and in a case where a difference between the grating reading and a target constant deviates from the range of the theoretical position $\Delta$, sending a correction command to the stepper motor and the driver by the control circuit to move the collimator to the station position where the collimator needs to move, and correcting angle deviation, so as to implement a second-stage closed-loop control; and after the stepper motor receives the motion command, repeatedly executing operations from the first-stage closed-loop control to the second-stage closed-loop control until the rotation seat assembly stops moving, and after the rotation seat assembly stops moving, the difference between the grating reading and the target constant being in the range of the theoretical position $\Delta$, and the electromagnetic push rod being locked in a hole and triggering a micro switch to return an in-place signal to the upper computer.

20. The motion control method according to claim 19, wherein the rotation seat assembly has two forward and reverse rotation over-range limit points, and completing the motor zero point initialization comprises:

detecting, by the control circuit, a relative position of the rotation seat assembly to the fixing seat by using a micro switch, setting a reverse rotation over-range limit point of the rotation seat assembly as a positioning origin, and searching for the positioning origin by using a press-contact mode:

controlling the rotation seat assembly to rotate reversely by the control circuit, determining a grating reading of an end face of the rotation seat assembly and a motor encoder reading to find the positioning origin, and rotating the rotation seat assembly forward after the positioning origin is determined, to allow all stations of the at least two collimators sequentially pass through the beam hole.

21. The motion control method according to claim 20, wherein using the grating position value of the preset position as the theoretical value of the preset position obtained by the primary position feedback mechanism comprises:

obtaining, by the control circuit, a motor stop bit END, and determining, whether the motor stop bit END is equal to 1; in response to the motor stop bit END being equal to 1, giving no alarm; and in response to the motor stop bit END being not equal to 1, stopping operation of the stepper motor and feeding back alarm information; and in a case of no alarm, refreshing, by the control circuit, the grating reading of the stop position of the stepper motor, writing the grating reading as departure data into a register, automatically updating, by the stepper motor, the grating position value of the preset position according to the departure data, and using the grating position value of the preset position as the theoretical value of the preset position; and in a case of giving the alarm, refreshing, by the control circuit, local alarm information with fed back alarm information, controlling and displaying the fed back alarm information, and reporting a data packet for processing, wherein the preset position comprises a plurality of stations; and in the case where the stepper motor stops moving according to the theoretical value of the preset position, and the grating reading of the stop position of the stepper motor fed back by the secondary position feedback mechanism is consistent with the theoretical value of the preset position, using the theoretical value of the preset position as the initial theoretical value of the motor comprises:

after the stepper motor executes a motion command to operate to each of the plurality of stations, verifying conformity between a grating reading of a stop position of the stepper motor and a theoretical value of the each of the plurality of stations, wherein the conformity comprises a comparison of a difference between the grating reading and the theoretical value with a preset difference range, and the motion command comprises the theoretical value of the each of the plurality of stations; and in response to the difference between the grating reading and the theoretical value being in the preset difference range, saving the grating reading as a position parameter of the each of the plurality of stations, and ending the motor initialization; and in response to the difference between the grating reading and the theoretical value not being in the preset difference range, executing initialization error reporting, setting an initialization failure mark, and ending the motor initialization.

* * * * *